United States Patent

Barker et al.

[11] Patent Number: 5,580,870
[45] Date of Patent: Dec. 3, 1996

[54] QUINAZOLINE DERIVATIVES

[75] Inventors: Andrew J. Barker, Macclesfield; Dearg S. Brown, Wilmslow, both of United Kingdom

[73] Assignee: Zeneca Limited, London, United Kingdom

[21] Appl. No.: 164,725

[22] Filed: Dec. 10, 1993

[30] Foreign Application Priority Data

Dec. 10, 1992 [GB] United Kingdom .................. 9225765
May 18, 1993 [GB] United Kingdom .................. 9310248

[51] Int. Cl.$^6$ .............. A61K 31/505; C07D 239/95; C07D 239/78; C07D 239/84
[52] U.S. Cl. ............. 514/234.5; 514/249; 514/259; 514/267; 544/119; 544/250; 544/284; 544/293
[58] Field of Search .................. 514/234.5, 249, 514/259, 267; 544/119, 250, 284, 293

[56] References Cited

U.S. PATENT DOCUMENTS 3,470,182  9/1969  Hardtmann et al. .................. 514/259

FOREIGN PATENT DOCUMENTS 0520722  12/1992  European Pat. Off. .
0566226  10/1993  European Pat. Off. .
9214716   9/1992  WIPO .
9220642  11/1992  WIPO .

OTHER PUBLICATIONS

Hiroshi; "On The Animation Of Azaheterocycles" Chemical Abstracts, 1983, vol. 98, p. 577, 143376M.
Burke, Jr; "Protein–Tyrosine Kinase Inhibitors", Drugs Of The Future, 1992, vol. 17, No. 2, pp. 119–131.
Mingli; "Synthesis and Antimalarial Activity of 2–Dialkylaminomethyl–4–(Heterocyclic Amino)–5, 6, 7, 8–Tetrahydronophthol Derivatives", Chemical Abstracts 1985, vol. 103 pp. 597–598, 87753q.

*Primary Examiner*—Mukund J. Shah
*Assistant Examiner*—Matthew V. Grumbling
*Attorney, Agent, or Firm*—Cushman Darby & Cushman, L.L.P.

[57]  ABSTRACT

The invention concerns quinazoline derivatives of the formula I

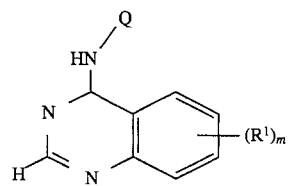

wherein m is 1, 2 or 3 and each $R^1$ includes hydroxy, amino, ureido, hydroxyamino, trifluoromethoxy, (1–4C)alkyl, (1–4C)alkoxy and (1–3C)alkylenedioxy; and Q is a 9- or 10-membered bicyclic heterocyclic moiety containing one or two nitrogen heteroatoms and optionally containing a further heteroatom selected from nitrogen, oxygen and sulphur, or Q is a 9- or 10-membered bicyclic aryl moiety which heterocyclic or aryl moiety may optionally bear one or two substituents selected from halogeno, hydroxy, oxo, amino, nitro, carbamoyl, (1–4C)alkyl, (1–4C)alkoxy, (1–4C)alkylamino, di-[(1–4C)alkyl]amino and (2–4C)alkanoylamino; or a pharmaceutically-acceptable salt thereof; processes for their preparation; pharmaceutical compositions containing them; and the use of the receptor tyrosine kinase inhibitory properties of the compounds in the treatment of cancer.

12 Claims, No Drawings

QUINAZOLINE DERIVATIVES

The invention relates to quinazoline derivatives, or pharmaceutically-acceptable salts thereof, which possess anti-cancer activity and are accordingly useful in methods of treatment of cancer in the human or animal body. The invention also relates to processes for the manufacture of said quinazoline derivatives, to pharmaceutical compositions containing them and to their use in the manufacture of medicaments of use in the production of an anti-cancer effect in a warm-blooded animal such as man.

Many of the current treatment regimes for cancer utilise compounds which inhibit DNA synthesis. Such compounds are toxic to cells generally but their toxic effect on the rapidly dividing tumour cells can be beneficial. Alternative approaches to anti-cancer agents which act by mechanisms other than the inhibition of DNA synthesis have the potential to display enhanced selectivity of action against cancer cells.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1 91). Several such oncogenes give rise to the production of peptides which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al. *Ann. Reports in Med. Chem.* 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor and an intracellular portion which functions as a kinase to phosphorylate tyrosine amino acids in proteins and hence to influence cell proliferation. It is known that such kinases are frequently present in common human cancers such as breast cancer (Sainsbury et al., *Brit. J. Cancer,* 1988, 58, 458; Guerin et al., *Oncogene Res.*, 1988, 3, 21), gastrointestinal cancer such as colon, rectal or stomach cancer (Bolen et al., *Oncogene Res.*, 1987, 1, 149), leukaemia (Konaka et al., *Cell,* 1984, 37, 1035) and ovarian, bronchial or pancreatic cancer (European Patent Specification No. 0400586). As further human tumour tissues are tested for receptor tyrosine kinase activity it is expected that its widespread prevalance will be established in further cancers such as thyroid and uterine cancer. It is also known that tyrosine kinase activity is rarely detected in normal cells whereas it is more frequently detectable in malignant cells (Hunter, *Cell,* 1987, 50, 823). It has been shown more recently (W J Gullick, *Brit. Med. Bull.,* 1991, 47, 87) that epidermal growth factor receptor which possesses tyrosine kinase activity is overexpressed in many human cancers such as brain, lung squamous cell, bladder, gastric, breast, head and neck, oesophageal, gynaecological and thyroid tumours.

Accordingly it has been recognised that an inhibitor of receptor tyrosine kinase should be of value as a selective inhibitor of the growth of mammalian cancer cells (Yaish et al. *Science,* 1988, 242, 933). Support for this view is provided by the demonstration that erbstatin, a receptor tyrosine kinase inhibitor, specifically attenuates the growth in athymic nude mice of a transplanted human mammary carcinoma which expresses epidermal growth factor (EGF) receptor tyrosine kinase but is without effect on the growth of another carcinoma which does not express EGF receptor tyrosine kinase (Toi et al., *Eur. J. Cancer Clin. Oncol.,* 1990, 26, 722.) Various derivatives of styrene are also stated to possess tyrosine kinase inhibitory properties (European Patent Application Nos. 0211363, 0304493 and 0322738) and to be of use as anti-tumour agents. The in vivo inhibitory effect of two styrene derivatives has been demonstrated against the growth of human squamous cell carcinoma inoculated into nude mice (Yoneda et al., *Cancer Research* 1991, 51, 4430). Accordingly it has been indicated that receptor tyrosine kinase inhibitors will prove to be useful in the treatment of a variety of human cancers. Various known tyrosine kinase inhibitors are disclosed in a more recent review by T R Burke Jr. (*Drugs of the Future,* 1992, 17, 119).

We have now found that certain quinazoline derivatives possess anti-cancer properties which are believed to arise from their receptor tyrosine kinase inhibitory properties.

It is known from the patent application WO 92/20642 that certain aryl and heteroaryl compounds inhibit receptor tyrosine kinase. There is the disclosure of certain quinazoline derivatives but no mention is made of 4-heteroarylaminoquinazoline derivatives.

It is disclosed in copending European Patent Application No. 92305703.8 (publication no. 0 520 722) and European Patent Application No. 93300270.1 (publication no. 0 566 226) that certain 4-anilinoquinazoline derivatives are useful as inhibitors of receptor tyrosine kinase.

It is known from *J. Het. Chem.,* 1982, 19, 1285 that a compound assigned the structure of 4,4'-diquinazolylamine [alternatively named as 4-(4-quinazolinylamino)quinazoline] is formed as a minor biproduct upon the amination of quinazoline.

According to one aspect of the invention there is provided a quinazoline derivative of the formula I

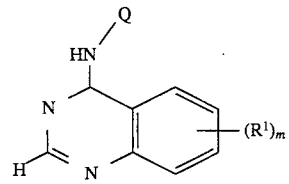

wherein m is 1, 2 or 3 and each $R^1$ is independently hydroxy, amino, ureido, hydroxyamino, trifluoromethoxy, (1–4C)alkyl, (1–4C)alkoxy, (1–3C)alkylenedioxy, (1–4C)alkylamino, di-[(1–4C)alkyl]amino, pyrrolidin-1-yl, piperidino, morpholino, piperazin-1-yl, 4-(1–4C)alkylpiperazin-1-yl, (1–4C)alkylthio, halogeno-(1–4C)alkyl, hydroxy-(1–4C)alkyl, (2–4C)alkanoyloxy-(1–4C)alkyl, (1–4C)alkoxy-(1–4C)alkyl, cyano-(1–4C)alkyl, amino-(1–4C)alkyl, (1–4C)alkylamino-(1–4C)alkyl, di-[(1–4C)alkyl]amino-(1–4C)alkyl, piperidino-(1–4C)alkyl, morpholino-(1–4C)alkyl, piperazin-1-yl-(1–4C)alkyl, 4-(1–4C)alkylpiperazin-1-yl-(1–4C)alkyl, hydroxy-(2–4C)alkoxy-(1–4C)alkyl, (1–4C)alkoxy-(2–4C)alkoxy-(1–4C)alkyl, hydroxy-(2–4C)alkylamino-(1–4C)alkyl, (1–4C)alkoxy-(2–4C)alkylamino-(1–4C)alkyl, halogeno-(2–4C)alkoxy, hydroxy-(2–4C)alkoxy, (2–4C)alkanoyloxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, (2–4C)alkanoyloxy, hydroxy-(2–4C)alkanoyloxy, (1–4C)alkoxy-(2–4C)alkanoyloxy, phenyl-(1–4C)alkoxy, halogeno-(2–4C)alkylamino, hydroxy-(2–4C)alkylamino, (2–4C)alkanoyloxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, (2–4C)alkanoylamino, (1–4C)alkoxycarbonylamino, benzamido, 3-phenylureido, halogeno-(2–4C)alkanoylamino, hydroxy-(2–4C)alkanoylamino or (1–4C)alkoxy-(2–4C)alkanoylamino, and wherein said benzamido substituent or any phenyl group in a $R^1$ substituent may optionally bear one or two halogeno, (1–4C)alkyl or (1–4C)alkoxy substituents; and Q is a 9- or 10-membered bicyclic heterocyclic moiety, or a hydrogenated derivative thereof, containing one or two nitrogen heteroatoms and optionally containing a further heteroatom selected from nitrogen, oxygen and sulphur, or Q is a 9- or 10-membered bicyclic aryl moiety, or a hydrogenated derivative thereof, which heterocyclic or aryl moiety, or hydrogenated derivatives thereof, may optionally bear one or two substituents selected from halogeno, hydroxy, oxo, amino, nitro, carbamoyl, (1–4C)alkyl, (1–4C)alkoxy, (1–4C)alkylamino, di-[(1–4C)alkyl]amino and (2–4C)alkanoylamino; or a pharmaceutically-acceptable salt thereof.

According to a further aspect of the invention there is provided a quinazoline derivative of the formula I as defined hereinbefore wherein in addition $R^1$ may be hydrogen, halogeno or nitro; and wherein in addition the optional one or two substituents on Q may be selected from carboxy and (1–4C)alkoxycarbonyl; or a pharmaceutically-acceptable salt thereof; except that 4-(4-quinazolinylamino)quinazoline is excluded.

According to a further aspect of the invention there is provided a quinazoline derivative of the formula I as defined hereinbefore wherein in addition $R^1$ may be 2-oxopyrrolidin-1-yl or 2-oxopiperidin-1-yl; and wherein in addition the optional one or two substituents on Q may be cyano; or a pharmaceutically-acceptable salt thereof; except that 4-(4-quinazolinylamino)quinazoline is excluded.

In this specification the term "alkyl" includes both straight and branched chain alkyl groups but references to individual alkyl groups such as "propyl" are specific for the straight chain version only. An analogous convention applies to other generic terms.

The quinazolines of the formula I are unsubstituted at the 2-position. This is specifically indicated in formula I by the hydrogen atom at the 2-position. It is to be understood that the $R^1$ groups are located only on the benzo portion of the quinazoline ring.

Within the present invention it is to be understood that a quinazoline derivative of the formula I as defined herein may exhibit the phenomenon of tautomerism and that the chemical names within this specification represent only one of the possible tautomeric forms. It is to be understood that the present invention encompasses any tautomeric form which possesses anti-cancer activity and is not to be limited merely to any one tautomeric form which has been specified within the specification.

It is also to be understood that certain quinazolines of the formula I can exist in solvated as well as unsolvated forms such as, for example, hydrated forms. It is to be understood that the invention encompasses all such solvated forms which possess anti-cancer activity.

Suitable values for the generic radicals referred to above include those set out below.

A suitable value for $R^1$ when it is (1–4C)alkyl is, for example, methyl, ethyl, propyl, isopropyl, butyl, isobutyl, sec-butyl or tert-butyl; when it is (1–4C)alkoxy is, for example, methoxy, ethoxy, propoxy, isopropoxy or butoxy; when it is (1–4C)alkylamino is, for example, methylamino, ethylamino or propylamino; when it is di-[(1–4C)alkyl]amino is, for example, dimethylamino, N-ethyl-N-methylamino, diethylamino, N-methyl-N-propylamino or dipropylamino; and when it is (1–4C)alkylthio is, for example, methylthio, ethylthio or propylthio.

Suitable values for each $R^1$ substituent which may be present on the quinazoline ring include, for example:

| | |
|---|---|
| for halogeno: | fluoro, chloro and bromo; |
| for (1–3C)alkylenedioxy: | methylenedioxy, ethylenedioxy and propylenedioxy; |
| for 4-(1–4C)alkylpiperazin-1-yl: | 4-methylpiperazin-1-yl and 4-ethylpiperazin-1-yl; |
| for halogeno-(1–4C)alkyl: | fluoromethyl, chloromethyl, bromomethyl, difluoromethyl, trifluoromethyl, dichloromethyl, dibromomethyl, 2-fluoroethyl, 2-chloroethyl and 2-bromoethyl; |
| for hydroxy-(1–4C)alkyl: | hydroxymethyl, 1-hydroxyethyl, 2-hydroxyethyl and 3-hydroxypropyl; |
| for (2–4C)alkanoyloxy-(1–4C)alkyl: | acetoxymethyl, propionyloxymethyl, butyryloxymethyl, 2-acetoxyethyl and 3-acetoxypropyl; |
| for (1–4C)alkoxy-(1–4C)alkyl: | methoxymethyl, ethoxymethyl, 1-methoxyethyl, 2-methoxyethyl, 2-ethoxyethyl and 3-methoxypropyl; |
| for cyano-(1–4C)alkyl: | cyanomethyl, 2-cyanomethyl and 3-cyanopropyl; |
| for amino-(1–4C)alkyl: | aminomethyl, 1-aminoethyl, 2-aminoethyl and 3-aminopropyl; |
| for (1–4C)alkylamino-(1–4C)alkyl: | methylaminomethyl, ethylaminomethyl, 1-methylaminoethyl, 2-methylaminoethyl, 2-ethylamimoethyl and 3-methylaminopropyl; |
| for di-[(1–4C)alkyl]amino-(1–4C)alkyl: | dimethylaminomethyl, diethylaminomethyl, 1-dimethylaminoethyl, 2-dimethylaminoethyl and 3-dimethylaminopropyl; |
| for piperidino-(1–4C)alkyl: | piperidinomethyl and 2-piperidinoethyl; |
| for morpholino-(1–4C)alkyl: | morpholinomethyl and 2-morpholinoethyl; |
| for piperazin-1-yl-(1–4C)alkyl: | piperazin-1-ylmethyl and 2-(piperazin-1-yl)ethyl; |
| for 4-(1–4C)alkylpiperazin-1-yl-(1–4C)alkyl: | 4-methylpiperazin-1-ylmethyl, 4-ethylpiperazin-1-ylmethyl, 2-(4-methylpiperazin-1-yl)ethyl and 2-(4-ethylpiperazin-1-yl)ethyl; |
| for hydroxy-(2–4C)alkoxy-(1–4C)alkyl: | 2-hydroxyethoxymethyl, 3-hydroxypropoxymethyl, 2-(2-hydroxyethoxy)ethyl and 2-(3-hydroxypropoxy)ethyl; |
| for (1–4C)alkoxy-(2–4C)alkoxy-(1–4C)alkyl: | 2-methoxyethoxymethyl, 2-ethoxyethoxymethyl, 3-methoxypropoxymethyl, 3-ethoxypropoxymethyl, 2-(2-methoxyethoxy)ethyl and 2-(2-ethoxyethoxy)ethyl; |
| for hydroxy-(2–4C)alkylamino-(1–4C)alkyl: | 2-hydroxyethylaminomethyl, 3-hydroxypropylaminomethyl, 2-(2-hydroxyethylamino)ethyl and 2-(3-hydroxypropylamino)ethyl; |
| for (1–4C)alkoxy-(2–4C)alkylamino-(1–4C)alkyl: | 2-methoxyethylaminomethyl, 2-ethoxyethylaminomethyl, 3-methoxypropylaminomethyl, 2-(2-methoxyethylamino)ethyl and 2-(2-ethoxyethylamino)ethyl; |
| for halogeno-(2–4C)alkoxy: | 2-fluoroethoxy, 2-chloroethoxy, 2-bromoethoxy, 3-fluoropropoxy and 3-chloropropoxy; |
| for hydroxy-(2–4C)alkoxy: | 2-hydroxyethoxy, 3-hydroxypropoxy and 4-hydroxybutoxy; |
| for (2–4C)alkanoyloxy-(2–4C)alkoxy: | 2-acetoxyethoxy, 2-propionyloxyethoxy, 2-butyryloxyethoxy and 3-acetoxypropoxy; |
| for (1–4C)alkoxy-(2–4C)alkoxy: | 2-methoxyethoxy, 2-ethoxyethoxy, 3-methoxypropoxy and 4-methoxybutoxy; |
| for amino-(2–4C)alkoxy: | 2-aminoethoxy and 3-aminopropoxy; |

| | |
|---|---|
| for (1–4C)alkylamino-(2–4C)alkoxy: | 2-methylaminoethoxy, 2-ethylaminoethoxy, 2-propylaminoethoxy, 3-methylaminopropoxy and 3-ethylaminopropoxy; |
| for di-[(1–4C)alkyl]amino-(2–4C)alkoxy: | 2-dimethylaminoethoxy, 2-(N-ethyl-N-methyl)ethoxy, 2-diethylaminoethoxy, 2-dipropylaminoethoxy, 3-dimethylaminopropoxy and 3-diethylaminopropoxy; |
| for (2–4C)alkanoyloxy: | acetoxy, propionyloxy and butyryloxy; |
| for hydroxy-(2–4C)alkanoyloxy: | 2-hydroxyacetoxy, 3-hydroxypropionyloxy and 4-hydroxybutyryloxy; |
| for (1–4C)alkoxy-(2–4C)alkanoyloxy: | 2-methoxyacetoxy, 2-ethoxyacetoxy and 3-methoxypropionyloxy; |
| for phenyl-(1–4C)alkoxy: | benzyloxy, 2-phenylethoxy and 3-phenylpropoxy; |
| for halogeno-(2–4C)alkylamino: | 2-fluoroethylamino, 2-chloroethylamino, 2-bromoethylamino, 3-fluoropropylamino and 3-chloropropylamino; |
| for hydroxy-(2–4C)alkylamino: | 2-hydroxyethylamino, 3-hydroxypropylamino and 4-hydroxybutylamino; |
| for (2–4C)alkanoyloxy-(2–4C)alkylamino: | 2-acetoxyethylamino, 2-propionyloxyethylamino, 2-butyryloxyethylamino and 3-acetoxypropylamino; |
| for (1–4C)alkoxy-(2–4C)alkylamino: | 2-methoxyethylamino, 2-ethoxyethylamino, 3-methoxypropylamino and 3-ethoxypropylamino; |
| for amino-(2–4C)alkylamino: | 2-aminoethylamino, 3-aminopropylamino and 4-aminobutylamino; |
| for (1–4C)alkylamino-(2–4C)alkylamino: | 2-methylaminoethylamino, 2-ethylaminoethylamino, 2-propylaminoethylamino, 3-methylaminopropylamino, 3-ethylaminopropylamino and 4-methylaminobutylamino; |
| for di-[(1–4C)alkyl]amino-(2–4C)alkylamino: | 2-dimethylaminoethylamino, 2-(N-ethyl-N-methylamino)ethylamino, 2-diethylaminoethylamino, 2-dipropylaminoethylamino, 3-dimethylaminopropylamino, 3-diethylaminopropylamino and 4-dimethylaminobutylamino; |
| for (2–4C)alkanoylamino: | acetamido, propionamido and butyramido; |
| for (1–4C)alkoxycarbonylamino: | methoxycarbonylamino, ethoxycarbonylamino and propoxycarbonylamino; |
| for halogeno-(2–4C)alkanoylamino: | 2-chloroacetamido, 2-bromoacetamido, 3-chloropropionamido and 3-bromopropionamido; |
| for hydroxy-(2–4C)alkanoylamino: | 2-hydroxyacetamido, 3-hydroxypropionamido and 4-hydroxybutyramido; and |
| for (1–4C)alkoxy-(2–4C)alkanoylamino: | 2-methoxyacetamido, 2-ethoxyacetamido, 2-propoxyacetamido, 3-methoxypropionamido, 3-ethoxypropionamido and 4-4-methoxybutyramido. |

When $R^1$ is (1–3C)alkylenedioxy the oxygen atoms of each such group occupy adjacent positions on the quinazoline ring.

Suitable values for the substituents which may be present on the phenyl ring when $R^1$ is benzamido, on a $R^1$ substituent which contains a phenyl group, or on Q include, for example:

| | |
|---|---|
| for halogeno: | fluoro, chloro and bromo; |
| for (1–4C)alkyl: | methyl, ethyl and propyl; |
| for (1–4C)alkoxy: | methoxy, ethoxy and propoxy; |
| for (1–4C)alkylamino: | methylamino, ethylamino and propylamino; |
| for di-[(1–4C)alkyl]amino: | dimethylamino, N-ethyl-N-methylamino and diethylamino; |
| for (2–4C)alkanoylamino: | acetamido, propionamido and butyramido; and |
| for (1–4C)alkoxycarbonyl: | methoxycarbonyl, ethoxycarbonyl and tert-butoxycarbonyl. |

A suitable value for Q when it is 9- or 10-membered bicyclic heterocyclic moiety, or a hydrogenated derivative thereof, containing one or two nitrogen heteroatoms and optionally containing a further heteroatom selected from nitrogen, oxygen and sulphur is, for example, a benzo-fused heterocyclic moiety, or a hydrogenated derivative thereof, such as indolyl, indolinyl, isoindolyl, isoindolinyl, indolizinyl, 1H-benzimidazolyl, 2,3-dihydro-1H-benzimidazolyl, 1H-indazolyl, 2,3-dihydro-1H-indazolyl, benzoxazolyl, 2,3-dihydrobenzoxazolyl, benzo[c]isoxazolyl, benzo[d]isoxazolyl, 2,3-dihydrobenzo[d]isoxazolyl, benzothiazolyl, 2,3-dihydrobenzothiazolyl, benzo[c]isothiazolyl, benzo[d]isothiazolyl, 2,3-dihydrobenzo[d]isothiazolyl, 1H-benzotriazolyl, benzo[c]furazanyl, benzo[c][2,1,3]thiadiazolyl, benzo[d][1,2,3]oxadiazolyl, benzo[d][1,2,3]thiadiazolyl, quinolyl, 1,2-dihydroquinolinyl, 1,2,3,4-tetrahydroquinolinyl, isoquinolyl, 1,2,3,4-tetrahydroisoquinolinyl, cinnolinyl, quinazolinyl, quinoxalinyl, phthalazinyl, 4H-1,4-benzoxazinyl, 2,3-dihydro-4H-1,4-benzoxazinyl, 4H-1,4-benzothiazinyl or 2,3-dihydro-4H,1,4-benzothiazinyl.

The heterocyclic moiety may be attached through any available position including from either of the two rings of the bicyclic heterocyclic moiety. The heterocyclic moiety may bear a suitable substituent such as a (1–4C)alkyl substituent on an available nitrogen atom. When the heterocyclic moiety is a hydrogenated derivative, the hydrogenated heterocyclic moiety may bear a suitable substituent such as an oxo substituent on an available carbon atom.

A suitable value for Q when it is a 9- or 10-membered bicyclic aryl moiety, or a hydrogenated derivative thereof, is, for example, indenyl, indanyl, naphthyl, 1,2-dihydronaphthyl or 1,2,3,4-tetrahydronaphthyl. The bicyclic aryl moiety may be attached through any available position including from either of the two rings. The bicyclic aryl moiety may bear a suitable substituent on either of the two rings. When the bicyclic aryl moiety is a hydrogenated derivative, the hydrogenated ring may bear a suitable substituent such as an oxo substituent on an available saturated carbon atom.

A suitable pharmaceutically-acceptable salt of a quinazoline derivative of the invention is, for example, an acid-addition salt of a quinazoline derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a quinazoline derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention include, for example, quinazoline derivatives of the formula I, or pharmaceutically-acceptable salts thereof, wherein:

(a) m is 1 or 2 and each $R^1$ is independently hydroxy, (1–4C)alkyl, (1–4C)alkoxy or (1–3C)alkylenedioxy; and Q has any of the meanings defined hereinbefore or in this section relating to particular novel compounds of the invention;

(b) m is 1 or 2 and each $R^1$ is independently hydroxy, amino, (1–4C)alkyl, (1–4C)alkoxy, (1–3C)alkylenedioxy, halogeno-(1–4C)alkyl, (1–4C)alkylamino-(1–4C)alkyl, di-[(1–4C)alkyl]amino-(1–4C)alkyl, piperidino-(1–4C)alkyl, morpholino-(1–4C)alkyl, piperazin-1-yl-(1–4C)alkyl, hydroxy-(2–4C)alkoxy, (1–4C)alkoxy-(2–4C)alkoxy, (1–4C)alkylamino-(2–4C)alkoxy, di-[(1–4C)alkyl]amino-(2–4C)alkoxy, hydroxy-(2–4C)alkylamino, (1–4C)alkoxy-(2–4C)alkylamino, (1–4C)alkylamino-(2–4C)alkylamino, di-[(1–4C)alkyl]amino-(2–4C)alkylamino, (2–4C)alkanoylamino, hydroxy-(2–4C)alkanoylamino or (1–4C)alkoxy-(2–4C)alkanoylamino; and Q has any of the meanings defined hereinbefore or in this section relating to particular novel compounds of the invention;

(c) m is 1 or 2 and each $R^1$ is independently hydroxy, (1–4C)alkoxy, (1–3C)alkylenedioxy, hydroxy-(2–4C)alkoxy, (1–4C)alkoxy-(2–4C)alkoxy or di-[(1–4C)alkyl]amino-(2–4C)alkoxy; and Q has any of the meanings defined hereinbefore or in this section relating to particular novel compounds of the invention;

(d) m is 1 or 2 and each $R^1$ is independently amino, hydroxy-(2–4C)alkylamino, (1–4C)alkoxy-(2–4C)alkylamino, di-[(1–4C)alkyl]amino-(2–4C)alkylamino, (2–4C)alkanoylamino, hydroxy-(2–4C)alkanoylamino or (1–4C)alkoxy-(2–4C)alkanoylamino; and Q has any of the meanings defined hereinbefore or in this section relating to particular novel compounds of the invention;

(e) m is 1, 2 or 3 and each $R^1$ is independently hydroxy, amino, ureido, hydroxyamino, trifluoromethoxy, (1–4C)alkyl, (1–4C)alkoxy, (1–3C)alkylenedioxy, (1–4C)alkylamino, di-[(1–4C)alkyl]amino, piperidino, morpholino, piperazin-1-yl, 4-(1–4C)alkylpiperazin-1-yl, (1–4C)alkylthio, halogeno-(1–4C)alkyl, (1–4C)alkoxy-(1–4C)alkyl, cyano-(1–4C)alkyl, (1–4C)alkylamino-(1–4C)alkyl, di-[(1–4C)alkyl]amino-(1–4C)alkyl, piperidino-(1–4C)alkyl, morpholino-(1–4C)alkyl, piperazin-1-yl-(1–4C)alkyl, hydroxy-(2–4C)alkoxy-(1–4C)alkyl, (1–4C)alkoxy-(2–4C)alkoxy-(1–4C)alkyl, halogeno-(2–4C)alkoxy, hydroxy-(2–4C)alkoxy, (1–4C)alkoxy-(2–4C)alkoxy, (1–4C)alkylamino-(2–4C)alkoxy, di-[(1–4C)alkyl]amino-(2–4C)alkoxy, (1–4C)alkoxy-(2–4C)alkanoyloxy, phenyl-(1–4C)alkoxy, hydroxy-(2–4C)alkylamino, (1–4C)alkoxy-(2–4C)alkylamino, (1–4C)alkylamino-(2–4C)alkylamino, di-[(1–4C)alkyl]amino-(2–4C)alkylamino, (2–4C)alkanoylamino, benzamido, 3-phenylureido, halogeno-(2–4C)alkanoylamino, hydroxy-(2–4C)alkanoylamino or (1–4C)alkoxy-(2–4C)alkanoylamino; and Q has any of the meanings defined hereinbefore or in this section relating to particular novel compounds of the invention;

(f) m is 1 or 2 and each $R^1$ is independently hydroxy, amino, ureido, trifluoromethoxy, (1–4C)alkyl, (1–4C)alkoxy, (1–3C)alkylenedioxy, (1–4C)alkylamino, di-[(1–4C)alkyl]amino, piperidino, morpholino, (1–4C)alkylthio, halogeno-(1–4C)alkyl, cyano-(1–4C)alkyl, halogeno-(2–4C)alkoxy, hydroxy-(2–4C)alkoxy, (1–4C)alkoxy-(2–4C)alkoxy, (1–4C)alkoxy-(2–4C)alkanoyloxy, phenyl-(1–4C)alkoxy, (1–4C)alkoxy-(2–4C)alkylamino, (2–4C)alkanoylamino, halogeno-(2–4C)alkanoylamino, 3-phenylureido or (1–4C)alkoxy-(2–4C)alkanoylamino; and Q has any of the meanings defined hereinbefore or in this section relating to particular novel compounds of the invention;

(g) m is 1 or 2 and each $R^1$ is independently hydroxy, amino, halogeno, nitro, (1–4C)alkoxy, (1–3C)alkylenedioxy, (1–4C)alkylamino, di-[(1–4C)alkyl]amino, pyrrolidin-1-yl, piperidino, morpholino, piperazin-1-yl, 4-(1–4C)alkylpiperazin-1-yl, (1–4C)alkylthio, (2–4C)alkanoylamino or halogeno-(2–4C)alkanoylamino; and Q has any of the meanings defined hereinbefore or in this section relating to particular novel compounds of the invention;

(h) Q is a 9- or 10-membered benzo-fused heterocyclic moiety, or a hydrogenated derivative thereof, containing one or two nitrogen heteroatoms and optionally containing a further heteroatom selected from nitrogen, oxygen and sulphur, which heterocyclic moiety may optionally bear one or two substituents selected from halogeno, hydroxy, oxo, amino, nitro, (1–4C)alkyl, (1–4C)alkoxy, (1–4C)alkylamino, di-[(1–4C)alkyl]amino and (2–4C)alkanoylamino; and m and $R^1$ have any of the meanings defined hereinbefore or in this section relating to particular novel compounds of the invention;

(i) Q is indolyl, isoindolyl, 1H-benzimidazolyl, 1H-indazolyl, benzoxazolyl, benzo[c]isoxazolyl, benzo[d]isoxazolyl, benzothiazolyl, benzo[c]isothiazolyl, benzo[d]isothiazolyl, 1H-benzotriazolyl, benzo[c]furazanyl, benzo[c][2,1,3]thiadiazolyl, quinolyl, isoquinolyl, cinnolinyl, quinazolinyl or quinoxalinyl, which heterocyclic moiety may optionally bear one or two substituents selected from halogeno, hydroxy, (1–4C)alkyl and (1–4C)alkoxy; and m and $R^1$ have any of the meanings defined hereinbefore or in this section relating to particular novel compounds of the invention;

(j) Q is indolinyl, isoindolinyl, 2,3-dihydro-1H-benzimidazolyl, 2,3-dihydro-1H-indazolyl, 2,3-dihydrobenzoxazolyl, 2,3-dihydrobenzo[d]isoxazolyl, 2,3-dihydrobenzothiazolyl, 2,3-dihydrobenzo[d]isothiazolyl, 1,2-dihydroquinolinyl, 1,2,3,4-tetrahydroquinolinyl, 1,2,3,4-tetrahydroisoquinolinyl, 2,3-dihydro-4H-1,4-benzoxazinyl or 2,3-dihydro-4H-1,4-benzothiazinyl, which hydrogenated heterocyclic moiety may optionally bear one or two substituents selected from halogeno, hydroxy, oxo, (1–4C)alkyl and (1–4C)alkoxy; and m and $R^1$ have any of the meanings defined hereinbefore or in this section relating to particular novel compounds of the invention;

(k) Q is indenyl, indanyl, naphthyl, 1,2-dihydronaphthyl or 1,2,3,4-tetrahydronaphthyl which may optionally bear one or two substituents selected from halogeno, hydroxy, oxo, (1–4C)alkyl and (1–4C)alkoxy; and m and $R^1$ have any of the meanings defined hereinbefore or in this section relating to particular novel compounds of the invention; or (l) Q is indenyl, indanyl or 1,2,3,4-tetrahydronaphthyl which may optionally bear one or two substituents selected from halogeno, hydroxy, oxo, (1–4C)alkyl and (1–4C)alkoxy; and m and $R^1$ have any of the meanings defined hereinbefore or in this section relating to particular novel compounds of the invention.

A preferred compound of the invention is a quinazoline derivative of the formula I wherein m is 1, 2 or 3 and each $R^1$ is independently hydroxy, amino, ureido, methyl, ethyl, methoxy, ethoxy, propoxy, isopropoxy, butoxy, methylenedioxy, ethylenedioxy, methylamino, ethylamino, dimethylamino, diethylamino, piperidino, morpholino, methoxymethyl, cyanomethyl, methoxyethoxymethyl, 2-bromoethoxy, 2-hydroxyethoxy, 3-hydroxypropoxy, 2-methoxyethoxy, 2-ethoxyethoxy, 3-methoxypropoxy, 3-ethoxypropoxy, 2-dimethylaminoethoxy, 2-diethylaminoethoxy, 2-methoxyacetoxy, benzyloxy, 2-hydroxyethylamino, 3-hydroxypropylamino, 2-methoxyethylamino, 2-ethoxyethylamino, 3-methoxypropylamino, 3-ethoxypropylamino, 2-dimethylaminoethylamino, 2-diethylaminoethylamino, 3-dimethylaminopropylamino, 3-diethylaminopropylamino, acetamido, propionamido, benzamido, 3-phenylureido, 2-chloroacetamido, 2-hydroxyacetamido, 2-methoxyacetamido or 2-ethoxyacetamido; and Q is indolyl, 1H-benzimidazolyl, 1H-indazolyl, benzoxazolyl, benzothiazolyl, 1H-benzotriazolyl, benzo[c]furazanyl, benzo[c][2,1,3]thiadiazolyl, quinolyl, isoquinolyl, cinnolinyl, quinazolinyl, quinoxalinyl, indenyl, indanyl or 1,2,3,4-tetrahydronaphthyl, which may optionally bear one or two substituents selected from fluoro, chloro, bromo, hydroxy, amino, methyl, ethyl, methoxy, ethoxy, methylamino, dimethylamino and acetamido; or a pharmaceutically-acceptable salt thereof.

A further preferred compound of the invention is a quinazoline derivative of the formula I wherein m is 1, 2 or 3 and each $R^1$ is independently hydroxy, amino, fluoro, chloro, nitro, methyl, ethyl, methoxy, ethoxy, propoxy, isopropoxy, butoxy, methylenedioxy, ethylenedioxy, methylamino, ethylamino, dimethylamino, diethylamino, pyrrolidin-1-yl, piperidino, morpholino, piperazin-1-yl, 4-methylpiperazin-1-yl, methylthio, ethylthio, acetamido, propionamido or 2-chloroacetamido; and Q is indolyl, 1H-benzimidazolyl, 1H-indazolyl, benzoxazolyl, benzothiazolyl, 1H-benzotriazolyl, benzo[c]furazanyl, benzo[c][2,1,3]thiadiazolyl, quinolyl, isoquinolyl, cinnolinyl, quinazolinyl, quinoxalinyl, indenyl, indanyl, naphthyl or 1,2,3,4-tetrahydronaphthyl, which may optionally bear one or two substituents selected from fluoro, chloro, hydroxy, amino, carboxy, methyl, ethyl, methoxy, ethoxy, methylamino, dimethylamino, acetamido, methoxycarbonyl and ethoxycarbonyl; or a pharmaceutically-acceptable salt thereof.

A further preferred compound of the invention is a quinazoline derivative of the formula I wherein $(R^1)_m$ is 6-hydroxy, 7-hydroxy, 6,7-dihydroxy, 6-amino, 7-amino, 6-methylamino, 6-dimethylamino, 6-piperidino, 7-piperidino, 6-morpholino, 7-morpholino, 6-methoxy, 7-methoxy, 6,7-dimethoxy, 6,7-diethoxy, 6-hydroxy-7-methoxy, 6-amino-7-methoxy, 6-amino-7-methylamino, 6-methoxy-7-isopropoxy, 6,7-methylenedioxy, 6,7-ethylenedioxy, 6-methoxymethyl, 6-cyanomethyl, 6-(2-methoxyethoxymethyl), 7-(2-hydroxyethoxy)-6-methoxy, 6,7-di-(2-hydroxyethoxy), 6-(2-methoxyethoxy), 6-methoxy-7-(2-methoxyethoxy), 6,7-di-(2-methoxyethoxy), 7-(2-bromoethoxy)-6-methoxy, 7-benzyloxy-6-methoxy, 6-(2-methoxyethylamino), 6-acetamido, 6-(2-chloroacetamido) or 6-(2-methoxyacetamido); and Q is 5-indolyl, 6-indolyl, 1H-benzimidazol-5-yl, 1H-benzimidazol-6-yl, 1H-indazol-5-yl, 1H-indazol-6-yl, 5-benzoxazolyl, 6-benzoxazolyl, 5-benzothiazolyl, 6-benzothiazolyl, 1H-benzotriazol-5-yl, 1H-benzotriazol-6-yl, benzo[c][2,1,3]thiadiazol-4-yl, 5-quinolyl, 6-quinolyl, 7-quinolyl, 8-quinolyl, 5-isoquinolyl, 6-isoquinolyl, 7-isoquinolyl, 8-isoquinolyl, 6-cinnolinyl, 7-cinnolinyl, 5-quinazolinyl, 6-quinazolinyl, 7-quinazolinyl, 8-quinazolinyl, 5-quinoxalinyl, 6-quinoxalinyl or 7-quinoxalinyl, which may optionally bear one or two substituents selected from fluoro, chloro, hydroxy, amino, methyl, methoxy, methylamino and acetamido; or Q is 4-indanyl, 5-indanyl, 1,2,3,4-tetrahydronaphth-5-yl, 1,2,3,4-tetrahydronaphth-6-yl or 1,2,3,4-tetrahydronaphth-7-yl which may optionally bear one or two substituents selected from fluoro, chloro, hydroxy, amino, methyl, methoxy, methylamino and acetamido; or a pharmaceuticaly-acceptable salt thereof.

A further preferred compound of the invention is a quinazoline derivative of the formula I wherein $(R^1)_m$ is 6-hydroxy, 7-hydroxy, 6,7-dihydroxy, 6-amino, 7-amino, 6-fluoro, 7-fluoro, 6-chloro, 7-chloro, 6-nitro, 6-methoxy, 7-methoxy, 6,7-dimethoxy, 6,7-diethoxy, 6-hydroxy-7-methoxy, 6,7-methylenedioxy, 6,7-ethylenedioxy, 6-methylamino, 7-methylamino, 6-ethylamino, 6-dimethylamino, 7-dimethylamino, 6-diethylamino, 6-pyrrolidin-1-yl, 7-pyrrolidin-1-yl, 6-piperidino, 7-piperidino, 6-morpholino, 7-morpholino, 6-piperazin-1-yl, 7-piperazin-1-yl, 6-(4-methylpiperazin-1-yl), 7-(4-methylpiperazin-1-yl), 6-methylthio, 7-methylthio, 6-amino-7-methoxy, 6-amino-7-methylamino, 6-acetamido, 7-acetamido, 6-(2-chloroacetamido) or 7-(2-chloroacetamido); and Q is 4-, 5- or 6-indolyl, 1H-benzimidazol-4-yl, 1H-benzimidazol-5-yl, 1H-benzimidazol-6-yl, 1H-indazol-4-yl, 1H-indazol-5-yl, 1H-indazol-6-yl, 1H-indazol-7-yl, 5- or 6-benzoxazolyl, 5- or 6-benzothiazolyl, 1H-benzotriazol-4-yl, 1H-benzotriazol-5-yl, 1H-benzotriazol-6-yl, benzo[c][2,1,3]thiadiazol-4-yl, 2-, 3-, 4-, 5-, 6-, 7- or 8-quinolyl, 1-, 3-, 4-, 5-, 6-, 7- or 8-isoquinolyl, 4-, 5-, 6-, 7- or 8-cinnolinyl, 5-, 6-, 7- or 8-quinazolinyl or 2-, 5- or 6-quinoxalinyl, which may optionally bear one or two substituents selected from fluoro, chloro, methyl, ethyl and methoxy; or Q is 4- or 5-indanyl, 1- or 2-naphthyl, 1,2,3,4-tetrahydronaphth-5-yl or 1,2,3,4-tetrahydronaphth-6-yl, which may optionally bear one or two substituents selected from fluoro, chloro, hydroxy, carboxy, methyl, methoxy and methoxycarbonyl; or a pharmaceutically-acceptable salt thereof.

A further preferred compound of the invention is a quinazoline derivative of the formula I wherein $(R^1)_m$ is 6-hydroxy, 7-hydroxy, 6,7-dihydroxy, 6-amino, 7-amino, 6-fluoro, 7-fluoro, 6-chloro, 7-chloro, 6-nitro, 6-methoxy, 7-methoxy, 6,7-dimethoxy, 6,7-diethoxy, 6-hydroxy-7-methoxy, 6,7-methylenedioxy, 6,7-ethylenedioxy, 6-methylamino, 7-methylamino, 6-ethylamino, 6-dimethylamino, 7-dimethylamino, 6-diethylamino, 6-pyrrolidin-1-yl, 7-pyrrolidin-1-yl, 6-piperidino, 7-piperidino, 6-morpholino, 7-morpholino, 6-piperazin-1-yl, 7-piperazin-1-yl, 6-(4-methylpiperazin-1-yl), 7-(4-methylpiperazin-1-yl), 6-methylthio, 7-methylthio, 6-amino-7-methoxy, 6-amino-7-methylamino, 6-acetamido, 7-acetamido, 6-(2-chloroacetamido), 7-(2-chloroacetamido), 6-(2-oxopyrrolidin-1-yl) or 7-(2-oxopyrrolidin-1-yl); and Q is 4-, 5- or 6-indolyl, 1H-benzimidazol-4-yl, 1H-benzimidazol-5-yl, 1H-benzimidazol-6-yl, 1H-indazol-4-yl, 1H-indazol-5-yl, 1H-indazol-6-yl, 1H-indazol-7-yl, 5- or 6-benzoxazolyl, 5- or 6-benzothiazolyl, 1H-benzotriazol-4-yl, 1H-benzotriazol-5-yl, 1H-benzotriazol-6-yl, benzo[c][2,1,3]thiadiazol-4-yl, benzo[c][2,1,3]thiadiazol-5-yl, 2-, 3-, 4-, 5-, 6-, 7- or 8-quinolyl, 1-, 3-, 4-, 5-, 6-, 7- or 8-isoquinolyl, 4-, 5-, 6-, 7- or 8-cinnolinyl, 5-, 6-, 7- or 8-quinazolinyl or 2-, 5- or 6-quinoxalinyl, which may optionally bear one or two substituents selected from fluoro, chloro, methyl, ethyl, methoxy and cyano; or Q is 4- or 5-indanyl, 1- or 2-naphthyl, 1,2,3,4-tetrahydronaphth-5-yl or 1,2,3,4-tetrahydronaphth-6-yl, which may optionally bear one or two substituents selected from fluoro, chloro, hydroxy, carboxy, methyl, methoxy and methoxycarbonyl; or a pharmaceutically-acceptable salt thereof.

A further preferred compound of the invention is a quinazoline derivative of the formula I wherein $(R^1)_m$ is 6-amino, 6,7-dimethoxy, 6-piperidino or 6-acetamido; and Q is 5-indolyl, 1H-indazol-5-yl, 6-benzothiazolyl, 1H-benzotriazol-5-yl, benzo[c][2,1,3]thiadiazol-4-yl, 5-quinolyl, 6-quinolyl, 8-quinolyl, 5-isoquinolyl or 5-quinoxalinyl; or a pharmaceutically-acceptable salt thereof.

A further preferred compound of the invention is a quinazoline derivative of the formula I wherein $(R^1)_m$ is 6-amino, 7-fluoro, 6-nitro, 6,7-dimethoxy, 6,7-methylenedioxy, 6-dimethylamino, 6-pyrrolidin-1-yl, 6-piperidino, 7-piperazin-1-yl, 7-methylthio, 6-acetamido or 6-(2-chloroacetamido); and Q is 4-, 5- or 6-indolyl, 1H-indazol-4-yl, 1H-indazol-5-yl, 1H-indazol-6-yl, 6-benzothiazolyl, 1H-benzotriazol-4-yl, benzo[c][2,1,3]thiadiazol-4-yl, 2-, 3-, 5-, 6-, 7- or 8-quinolyl, 1-, 5- or 8-isoquinolyl or 5-quinoxalinyl, which may optionally bear one or two substituents selected from methyl and methoxy; or a pharmaceutically-acceptable salt thereof.

A further preferred compound of the invention is a quinazoline derivative of the formula I wherein $(R^1)_m$ is 6-amino, 7-fluoro, 6-nitro, 6,7-dimethoxy, 6,7-methylenedioxy, 6-dimethylamino, 6-pyrrolidin-1-yl, 6-piperidino, 7-piperazin-1-yl, 7-methylthio, 6-acetamido, 6-(2-chloroacetamido) or 2-oxopyrrolidin-1-yl; and Q is 4-, 5- or 6-indolyl, 1H-indazol-4-yl, 1H-indazol-5-yl, 1H-indazol-6-yl, 6-benzothiazolyl, 1H-benzotriazol-4-yl, benzo[c][2,1,3]thiadiazol-4-yl, benzo[c][2,1,3]thiadiazol-5-yl, 2-, 3-, 5-, 6-, 7- or 8-quinolyl, 1-, 5- or 8-isoquinolyl or 5-quinoxalinyl, which may optionally bear one or two substituents selected from methyl, methoxy and cyano; or a pharmaceutically-acceptable salt thereof.

A further preferred compound of the invention is a quinazoline derivative of the formula I wherein $(R^1)_m$ is 6-amino, 6,7-dimethoxy, 6-piperidino or 6-acetamido; and Q is 4- or 5-indanyl or 1,2,3,4-tetrahydronaphth-5-yl; or a pharmaceutically-acceptable salt thereof.

A further preferred compound of the invention is a quinazoline derivative of the formula I wherein $(R^1)_m$ is 6-amino, 6,7-dimethoxy, 6-piperidino or 6-acetamido; and Q is 5-indanyl or 1,2,3,4-tetrahydronaphth-5-yl; or a pharmaceutically-acceptable salt thereof.

A specific preferred compound of the invention is the following quinazoline derivative of the formula I: 6,7-dimethoxy-4-(5-quinolylamino)quinazoline, 6,7-dimethoxy-4-(6-quinolylamino)quinazoline, 6,7-dimethoxy-4-(5-isoquinolylamino)quinazoline, 6,7-dimethoxy-4-(5-indolylamino)quinazoline, 6,7-dimethoxy-4-[(1H-indazol-5-yl)amino]quinazoline, 4-(6-benzothiazolylamino)-6,7-dimethoxyquinazoline or 4-[(benzo[c][2,1,3]thiadiazol-4-yl)amino]-6,7-dimethoxyquinazoline; or a pharmaceutically-acceptable acid-addition salt thereof.

A further specific preferred compound of the invention is the following quinazoline derivative of the formula I: 6-(2-chloroacetamido)-4-(6-quinolylamino)quinazoline, 6,7-dimethoxy-4-(8-quinolylamino)quinazoline, 6,7-dimethoxy-4-(8-isoquinolylamino)quinazoline, 6,7-dimethoxy-4-(3-quinolylamino)quinazoline, 6,7-dimethoxy-4-(1H-indazol-6-ylamino)quinazoline, 6,7-dimethoxy-4-(1H-indazol-4-ylamino)quinazoline, 4-(1H-indazol-5-ylamino)-6-(1-pyrrolidinyl)quinazoline, 6-dimethylamino-4-(5-indolylamino)quinazoline, 4-(5-indolylamino)-6-(1-pyrrolidinyl)quinazoline or 6,7-dimethoxy-4-(6-indolylamino)quinazoline; or a pharmaceutically-acceptable acid-addition salt thereof.

A further specific preferred compound of the invention is the following quinazoline derivative of the formula I: 6,7-dimethoxy-4-(5-indanylamino)quinazoline or 6,7-dimethoxy-4-[(1,2,3,4-tetrahydronaphth-5-yl)amino]quinazoline; or a pharmaceutically-acceptable acid-addition salt thereof.

A quinazoline derivative of the formula I, or a pharmaceutically-acceptable salt thereof, may be prepared by any process known to be applicable to the preparation of chemically-related compounds. Such processes, when used to prepare a quinazoline derivative of the formula I, or a pharmaceutically-acceptable salt thereof, are provided as a further feature of the invention and are illustrated by the following representative examples in which, unless otherwise stated, $R^1$, m and Q have any of the meanings defined hereinbefore for a quinazoline derivative of the formula I. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

(a) The reaction, conveniently in the presence of a suitable base, of a quinazoline of the formula II

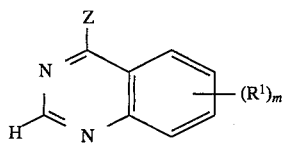

wherein Z is a displaceable group, with an amine of the formula $H_2N$—Q.

A suitable displaceable group Z is, for example, a halogeno, alkoxy, aryloxy or sulphonyloxy group, for example a chloro, bromo, methoxy, phenoxy, methanesulphonyloxy or toluene-p-sulphonyloxy group.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide. Alternatively a suitable base is, for example, an alkali metal or alkaline earth metal amide, for example sodium amide or sodium bis(trimethylsilyl)amide.

The reaction is preferably carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10° to 150° C., preferably in the range 20° to 80° C.

The quinazoline derivative of the formula I may be obtained from this process in the form of the free base or alternatively it may be obtained in the form of a salt with the acid of the formula H—Z wherein Z has the meaning defined hereinbefore. When it is desired to obtain the free base from the salt, the salt may be treated with a suitable base as defined hereinbefore using a conventional procedure.

(b) For the production of those compounds of the formula I wherein $R^1$ is amino, the reduction of a quinazoline derivative of the formula I wherein $R^1$ is nitro.

The reduction may conveniently be carried out by any of the many procedures known for such a transformation. The reduction may be carried out, for example, by the hydrogenation of a solution of the nitro compound in an inert solvent or diluent as defined hereinbefore in the presence of a suitable metal catalyst such as palladium or platinum. A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example, 50° to 150° C., conveniently at or near 70° C.

(c) For the production of those compounds of the formula I wherein $R^1$ is (2–4C)alkanoylamino or substituted (2–4C)alkanoylamino, benzamido, ureido or 3-phenylureido, the acylation of a quinazoline derivative of the formula I wherein $R^1$ is amino.

A suitable acylating agent is, for example, any agent known in the art for the acylation of amino to acylamino, for example an acyl halide, for example a (2–4C)alkanoyl chloride or bromide or a benzoyl chloride or bromide, conveniently in the presence of a suitable base, as defined hereinbefore, an alkanoic acid anhydride or mixed anhydride, for example a (2–4C)alkanoic acid anhydride such as acetic anhydride or the mixed anhydride formed by the reaction of an alkanoic acid and a (1–4C)alkoxycarbonyl halide, for example a (1–4C)alkoxycarbonyl chloride, in the presence of a suitable base as defined hereinbefore. For the production of those compounds of the formula I wherein $R^1$ is ureido or 3-phenylureido, a suitable acylating agent is, for example, a cyanate, for example an alkali metal cyanate such as sodium cyanate or, for example, an isocyanate such as phenyl isocyanate. In general the acylation is carried out in a suitable inert solvent or diluent as defined hereinbefore and at a temperature, in the range, for example, −30° to 120° C., conveniently at or near ambient temperature.

(d) For the production of those compounds of the formula I wherein $R^1$ is (1–4C)alkoxy or substituted (1–4C)alkoxy or $R^1$ is (1–4C)alkylamino or substituted (1–4C)alkylamino, the alkylation, preferably in the presence of a suitable base as defined hereinbefore, of a quinazoline derivative of the formula I wherein $R^1$ is hydroxy or amino as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1–4C)alkyl chloride, bromide or iodide or a substituted (1–4C)alkyl chloride, bromide or iodide, in the presence of a suitable base as defined hereinbefore, in a suitable inert solvent or diluent as defined hereinbefore and at a temperature in the range, for example, 10° to 140° C., conveniently at or near ambient temperature.

(e) For the production of those compounds of the formula I wherein $R^1$ is an amino-, oxy- or cyano-substituted (1–4C)alkyl substituent, the reaction, preferably in the presence of a suitable base as defined hereinbefore, of a quinazoline derivative of the formula I wherein $R^1$ is a (1–4C)alkyl substituent bearing a displaceable group as defined hereinbefore with an appropriate amine, alcohol or cyanide.

The reaction is preferably carried out in a suitable inert solvent or diluent as defined hereinbefore and at a temperature in the range, for example, 10° to 100° C., conveniently at or near ambient temperature.

(f) For the production of those compounds of the formula I wherein $R^1$ is amino, (1–4C)alkylamino, di-[(1–4C)alkyl] amino, pyrrolidin-1-yl, piperidino, morpholino, piperazin-1-yl, 4-(1–4C)alkylpiperazin-1-yl or (1–4C)alkylthio, the reaction, conveniently in the presence of a suitable base as defined hereinbefore, of a quinazoline derivative of the formula I wherein $R^1$ is a displaceable group as defined hereinbefore with an appropriate amine or thiol.

The reaction is preferably carried out in a suitable inert solvent or diluent as defined hereinbefore and at a temperature in the range, for example, 10° to 180° C., conveniently in the range 100° to 150° C.

(g) For the production of those compounds of the formula I wherein $R^1$ is 2-oxopyrrolidin-1-yl or 2-oxopiperidin-1-yl, the cyclisation, conveniently in the presence of a suitable base as defined hereinbefore, of a quinazoline derivative of the formula I wherein $R^1$ is a halogen-(2–4C)alkanoylamino group.

The reaction is preferably carried out in a suitable inert solvent or diluent as defined hereinbefore and at a temperature in the range, for example, 10° to 100° C. conveniently at or near ambient temperature.

When a pharmaceutically-acceptable salt of a quinazoline derivative of the formula I is required, for example an acid-addition salt of a quinazoline derivative of the formula I, it may be obtained, for example, by reaction of said compound with, for example, a suitable acid using a conventional procedure.

As stated hereinbefore the quinazoline derivative defined in the present invention possesses anti-cancer activity which is believed to arise from the receptor tyrosine kinase inhibitory activity of the compound. These properties may be assessed, for example, using one or more of the procedures set out below:

(a) An in vitro assay which determines the ability of a test compound to inhibit the enzyme receptor tyrosine kinase. Receptor tyrosine kinase was obtained in partially purified form from A-431 cells (derived from human vulval carcinoma) by procedures related to those described by Carpenter et al., *J. Biol. Chem.*, 1979, 254, 4884, Cohen et al., *J. Biol. Chem.*, 1982, 257, 1523 and by Braun et al., *J. Biol. Chem.*, 1984, 259, 2051.

A-431 cells were grown to confluence using Dulbecco's modified Eagle's medium (DMEM) containing 5% fetal calf serum (FCS). The obtained cells were homogenised in a hypotonic borate/EDTA buffer at pH 10.1. The homogenate was centrifuged at 400 g for 10 minutes at 0°–4° C. The supernatant was centrifuged at 25,000 g for 30 minutes at 0°–4° C. The pelleted material was suspended in 30 mM Hepes buffer at pH 7.4 containing 5% glycerol, 4 mM benzamidine and 1% Triton X-100, stirred for 1 hour at 0°–4° C., and recentrifuged at 100,000 g for 1 hour at 0°–4° C. The supernatant, containing solubilised receptor tyrosine kinase, was stored in liquid nitrogen.

For test purposes 40 µl of the enzyme solution so obtained was added to a mixture of 400 µl of a mixture of 150 mM Hepes buffer at pH 7.4, 500 µM sodium orthovanadate, 0.1% Triton X-100, 10% glycerol, 200 µl water, 80 µl of 25 mM DTT and 80 µl of a mixture of 12.5 mM manganese chloride, 125 mM magnesium chloride and distilled water. There was thus obtained the test enzyme solution.

Each test compound was dissolved in dimethylsulphoxide (DMSO) to give a 50 mM solution which was diluted with 40 mM Hepes buffer containing 0.1% Triton X-100, 10% glycerol and 10% DMSO to give a 500 µM solution. Equal volumes of this solution and a solution of epidermal growth factor (EGF; 20 µg/ml) were mixed.

[γ-$^{32}$P]ATP (3000 Ci/mM, 250 µCi) was diluted to a volume of 2 ml by the addition of a solution of ATP (100 µM) in distilled water. An equal volume of a 4 mg/ml solution of the peptide Arg-Arg-Leu-Ile-Glu-Asp-Ala-Glu-Tyr-Ala-Ala-Arg-Gly in a mixture of 40 mM Hepes buffer at pH 7.4, 0.1% Triton X-100 and 10% glycerol was added.

The test compound/EGF mixture solution (5 µl) was added to the test enzyme solution (10 µl) and the mixture was incubated at 0°–4° C. for 30 minutes. The ATP/peptide mixture (10 µl) was added and the mixture was incubated at 25° C. for 10 minutes. The phosphorylation reaction was terminated by the addition of 5% trichloroacetic acid (40 µl) and bovine serum albumin (BSA; 1 mg/ml, 5 µl). The mixture was allowed to stand at 4° C. for 30 minutes and then centrifuged. An aliquot (40 μl) of the supernatant was placed onto a strip of Whatman p 81 phosphocellulose paper. The strip was washed in 75 mM phosphoric acid (4×10 ml) and blotted dry. Radioactivity present in the filter paper was measured using a liquid scintillation counter (Sequence A). The reaction sequence was repeated in the absence of the EGF (Sequence B) and again in the absence of the test compound (Sequence C).

Receptor tyrosine kinase inhibition was calculated as follows:

$$\% \text{ Inhibition} = \frac{100 - (A - B)}{C - B} \times 100$$

The extent of inhibition was then determined at a range of concentrations of test compound to give an $IC_{50}$ value.

(b) An in vitro assay which determines the ability of a test compound to inhibit the growth of the human naso-pharyngeal cancer cell line KB.

KB cells were seeded into wells at a density of $1 \times 10^4 - 1.5 \times 10^4$ cells per well and grown for 24 hours in DMEM supplemented with 5% FCS (charcoal-stripped). Cell growth was determined after incubation for 3 days by the extent of metabolism of MTT tetrazolium dye to furnish a bluish colour. Cell growth was then determined in the presence of EGF (10 ng/ml) or in the presence of EGF (10 ng/ml) and a test compound at a range of concentrations. An $IC_{50}$ value could then be calculated.

(c) An in vivo assay in a group of male rats which determines the ability of a test compound (usually administered orally as a ball-milled suspension in 0.5% polysorbate) to inhibit the stimulation of liver hepatocyte growth caused by the administration of the growth factor TGFα (400 μg/kg subcutaneously, usually dosed twice, 3 and 7 hours respectively after the administration of the test compound).

In a control group of rats, the administration of TGFα causes on average a 5-fold stimulation of liver hepatocyte growth.

Cell-growth in the control and test animals is determined as follows:

On the morning of the day after the dosing of the test compound (or 0.5% polysorbate in the control group), the animals are dosed with bromodeoxyuridine (BrdU; 100 mg/kg intraperitoneally). The animals are killed four hours later and the livers are excised. Slices are cut from each liver and the uptake of BrdU is determined by a conventional immunohistochemical technique similar to that described on pages 267 and 268 of an article by Goldsworthy et al. in Chemically Induced Cell Proliferation: Implications for Risk Assessment, Wiley-Liss Inc., 1991, pages 253–284. Further tests were carried out using a range of doses of the test compounds to allow the calculation of an approximate $ED_{50}$ value for the inhibition of liver hepatocyte proliferation as determined by inhibition of the uptake of BrdU.

Although the pharmacological properties of the compounds of the formula I vary with structural change as expected, in general activity possessed by compounds of the formula I may be demonstrated at the following concentrations or doses in one or more of the above Tests (a), (b) and (c):

Test (a): $IC_{50}$ in the range, for example, 0.0005–1 μM;

Test (b): $IC_{50}$ in the range, for example, 0.01–10 μM.

Test (c): $ED_{50}$ in the range, for example, 1–100 mg/kg.

Thus, by way of example, the compound 6,7-dimethoxy-4-(5-quinolylamino)quinazoline has an $IC_{50}$ of 0.06 μM in Test (a), an $IC_{50}$ of 1.8 μM in Test (b) and an $ED_{50}$ of approximately 2 mg/kg in Test (c); the compound 6,7-dimethoxy-4-(5-indolylamino)quinazoline has an $IC_{50}$ of 0.001 μM in Test (a), an $IC_{50}$ of 0.4 μM in Test (b) and an $ED_{50}$ in the range 1 to 5 mg/kg in Test (c); and the compound 6,7-dimethoxy-4-(5-indanylamino)quinazoline has an $IC_{50}$ of 0.14 μM in Test (a), an $IC_{50}$ of 0.65 μM in Test (b) and an $ED_{50}$ in the range 1 to 5 mg/kg in Test (c).

According to a further aspect of the invention there is provided a pharmaceutical composition which comprises a quinazoline derivative of the formula I, or a pharmaceutically-acceptable salt thereof, as defined hereinbefore in association with a pharmaceutically-acceptable diluent or carrier.

The composition may be in a form suitable for oral administration, for example as a tablet or capsule, for parenteral injection (including intraveous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The quinazoline will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a quinazoline derivative of the formula I as defined hereinbefore for use in a method of treatment of the human or animal body by therapy.

We have now found that the compounds of the present invention possess anti-cancer properties which are believed to arise from their receptor tyrosine kinase inhibitory activity. Accordingly the compounds of the present invention are expected to be useful in the treatment of diseases or medical conditions mediated alone or in part by the enzyme receptor tyrosine kinase, i.e. the compounds may be used to produce a receptor tyrosine kinase inhibitory effect in a warm-blooded animal in need of such treatment. Thus the compounds of the present invention provide a method for treating the proliferation of malignant cells characterised by inhibition of the enzyme receptor tyrosine kinase, i.e. the compounds may be used to produce an anti-proliferative effect mediated alone or in part by the inhibition of the enzyme receptor tyrosine kinase. Accordingly the compounds of the present invention are expected to be useful in the treatment of cancer by providing an anti-proliferative effect, particularly in the treatment of receptor tyrosine kinase sensitive cancers such as cancers of the breast, lung, colon, rectum, stomach, prostate, bladder, pancreas and ovary.

Thus according to this aspect of the invention there is provided the use of a quinazoline derivative of the formula I, or a pharmaceutically-acceptable salt thereof, as defined hereinbefore in the manufacture of a medicament for use in the production of an anti-cancer effect in a warm-blooded animal such as man.

According to a further feature of this aspect of the invention there is provided a method for producing an anti-cancer effect in a warm-blooded animal, such as man, in need of such treatment which comprises administering to said animal an effective amount of a quinazoline derivative as defined immediately above.

As stated above the size of the dose required for the therapeutic or prophylactic treatment of a particular cancer will necessarily be varied depending on the host treated, the route of administration and the severity of the illness being treated. A unit dose in the range, for example, 1–100 mg/kg, preferably 1–50 mg/kg is envisaged.

The anti-cancer treatment defined hereinbefore may be applied as a sole therapy or may involve, in addition to the quinazoline derivative of the invention, one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred antimetabolites disclosed in European Patent Application No. 239362 such as N-{5-[N-(3,4-dihydro-2-methyl-4-oxoquinazolin-6-ylmethyl)-N-methylamino]-2-thenoyl}-L-glutamic acid; intercalating antibiotics, for example adriamycin and bleomycin; enzymes, for example asparaginase; topoisomerase inhibitors, for example etoposide; biological response modifiers, for example interferon; and anti-hormones, for example anti-oestrogens such as 'NOLVADEX' (tamoxifen) or, for example antiandrogens such as 'CASODEX' (4'-cyano-3-(4-fluorophenylsulphonyl)-2-hydroxy-2-methyl-3'-(trifluoromethyl)propionanilide. Such conjoint treatment may be achieved by way of the simultaneous, sequential or separate dosing of the individual components of the treatment. According to this aspect of the invention there is provided a pharmaceutical product comprising a quinazoline derivative of the formula I as defined hereinbefore and an additional anti-tumour substance as defined hereinbefore for the conjoint treatment of cancer.

As stated above the quinazoline derivative defined in the present invention is an effective anti-cancer agent, which property is believed to arise from its receptor tyrosine kinase inhibitory properties. Such a quinazoline derivative of the invention is expected to possess a wide range of anti-cancer properties as receptor tyrosine kinases have been implicated in many common human cancers such as leukaemia and breast, lung, colon, rectal, stomach, prostate, bladder, pancreas and ovarian cancer. Thus it is expected that a quinazoline derivative of the invention will possess anti-cancer activity against these cancers. It is in addition expected that a quinazoline of the present invention will possess activity against a range of leukaemias, lymphoid malignancies and solid tumours such as carcinomas and sarcomas in tissues such as the liver, kidney, prostate and pancreas.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet;

(vii) intermediates were not generally fully characterised and purity was assessed by thin layer chromatography (TLC), infra-red (IR) or NMR analysis;

(viii) the following abbreviations have been used:

DMF N,N-dimethylformamide;

DMA N,N-dimethylacetamide;

THF tetrahydrofuran;

NMP N-methylpyrrolidin-2-one.

EXAMPLE 1

A mixture of 4-chloro-6,7-dimethoxyquinazoline (2.7 g), 5-aminoquinoline (2.3 g) and isopropanol (100 ml) was stirred and heated to reflux for 2 hours. The precipitate was filtered off and washed in turn with cold isopropanol, ethanol and acetone. The solid so obtained was stirred as a suspension in methanol (75 ml) and potassium carbonate (5 g) was added. The mixture was stirred at ambient temperature for 15 minutes. The mixture was filtered and the filtrate was evaporated. The residue was purified by column chromatography using a 25:2 mixture of methylene chloride and methanol as eluent. There was thus obtained 6,7-dimethoxy-4-(5-quinolylamino)quinazoline (1.41 g, 35%), m.p. >240° C.;

NMR Spectrum: ($CD_3SOCD_3$) 3.95 (s, 3H), 3.98 (s, 3H), 7.21 (s, 1H), 7.50 (m, 1H), 7.67 (d, 1H), 7.83 (m, 1H), 7.98 (s, 1H), 8.0 (d, 1H), 8.22 (s, 1H), 8.26 (d, 1H), 8.93 (m, 1H), 9.89 (broad s, 1H);

Elemental Analysis: Found C, 69.0; H, 4.7; N, 17.0; $C_{19}H_{16}N_4O_2$ requires C, 68.7; H, 4.85; N, 16.9%.

The 4-chloro-6,7-dimethoxyquinazoline used as a starting material was obtained as follows:

A mixture of 4,5-dimethoxyanthranilic acid (19.7 g) and formamide (10 ml) was stirred and heated to 190° C. for 5 hours. The mixture was allowed to cool to approximately 80° C. and water (50 ml) was added. The mixture was stored at ambient temperature for 3 hours. The precipitate was isolated, washed with water and dried. There was thus obtained 6,7-dimethoxyquinazolin-4-one (3.65 g).

A mixture of a portion (2.5 g) of the material so obtained, thionyl chloride (4.5 ml) and DMF (1 drop) was stirred and heated to reflux for 2 hours. The mixture was evaporated to give the required starting material as a solid (2.7 g).

EXAMPLE 2

Using an analogous procedure to that described in Example 1, 4-chloro-6,7-dimethoxyquinazoline was reacted with the appropriate heterocyclic amine to give the compounds described in the following table, the structures of which were confirmed by proton magnetic resonance spectroscopy and by elemental analysis.

TABLE I

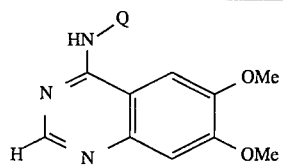

| Example 2 Compd. No. | Q | m.p. (°C.) |
|---|---|---|
| 1[a] | 6-quinolyl | >240 |
| 2[b] | 5-isoquinolyl | 133–136 |
| 3[c] | 8-quinolyl | 192–194 |
| 4[d] | 5-quinoxalinyl | 233–236 |
| 5[e] | 5-indolyl | 235–237 |
| 6[f,g] | 1H-indazol-5-yl | 241–242 |
| 7[f,h] | 1H-benzotriazol-5-yl | 244–246 |
| 8[f,i] | 6-benzothiazolyl | 265–268 |
| 9[f,j] | benzo[c][2,1,3]thiadiazol-4-yl | 257–259 |
| 10[k] | 5-indanyl | 242–243 |
| 11[l] | 1,2,3,4-tetrahydronaphth-5-yl | 254–256 |

Notes a. The product gave the following NMR data: ($CD_3SOCD_3$) 3.95 (s, 3H), 3.99 (s, 3H), 7.24 (s, 1H), 7.52 (m, 1H), 7.92 (s, 1H), 8.05 (d, 1H), 8.19 (m, 1H), 8.33 (d, 1H), 8.48 (d, 1H), 8.57 (s, 1H), 8.82 (m,1H), 9.28 (broad s. 1H);
and the following analytical data: Found C, 68.9; H, 4.8; N, 16.9; $C_{19}H_{16}N_4O_2$ requires C, 68.7; H, 4.85; N, 16.9%.

b. The product gave the following NMR data: ($CD_3SOCD_3$) 3.96 (s, 3H), 3.98 (s, 3H), 7.22 (s, 1H), 7.71 (d, 1H), 7.76 (t, 1H), 7.88 (d, 1H), 7.98 (s, 1H), 8.09 (d, 1H), 8.24 (s, 1H), 8.47 (d, 1H), 9.39 (s, 1H), 9.88 (broad s, 1H);
and the following analytical data: Found C, 67.4; H, 4.6; N, 16.5; $C_{19}H_{16}N_4O_2$ 0.25$H_2O$ requires C, 67.7; H, 4.9; N, 16.6%.

c. The product gave the following NMR data: ($CD_3SOCD_3$) 3.95 (s, 3H), 4.02 (s, 3H), 7.25 (s, 1H), 7.58–7.70 (m, 4H), 8.43 (m, 1H), 8.58 (s, 1H), 8.82 (m, 1H), 8.90 (m, 1H), 10.23 (broad s, 1H);
and the following analytical data: Found C, 68.3; H, 4.8; N, 16.5; $C_{19}H_{16}N_4O_2$ 0.05$H_2O$ requires C, 68.5; H, 4.9; N, 16.8%.

d. 5-Aminoquinoxaline is described in J. Chem. Soc., 1948, 2129. THF was used in place of isopropanol as the reaction solvent. The reaction mixture was heated to reflux for 4 hours. The product gave the following NMR data: ($CD_3SOCD_3$) 3.97 (s, 3H), 4.02 (s, 3H), 7.26 (s, 1H), 7.75 (s, 1H), 7.85–7.98 (m, 2H), 8.51 (s, 1H), 8.64 (d, 1H), 8.98 (d, 1H), 9.03 (d, 1H), 10.02 (broad s, 1H);
and the following analytical data: Found C, 63.7; H, 4.7; N, 20.6; $C_{18}H_{15}N_5O_2$ 0.35$H_2O$ requires C, 63.7; H, 4.5; N, 20.3%.

e. THF was used in place of isopropanol and the reaction mixture was heated to reflux for 4 hours. The product gave the following NMR data: ($CD_3SOCD_3$) 3.93 (s, 3H), 3.95 (s, 3H), 6.44 (t, 1H), 7.15 (s, 1H), 7.3–7.43 (m, 3H), 7.86 (s, 1H), 7.88 (s, 1H), 8.36 (s, 1H), 9.46 (broad s, 1H), 11.05 (broad s, 1H); and the following analytical data:
Found C, 67.2; H, 4.8; N, 17.6;
$C_{18}H_{16}N_4O_2$ requires C, 67.5; H, 5.0; N, 17.5%.

f. THF was used in place of isopropanol and the reaction mixture was heated to reflux for 20 hours. The initial precipitate, the hydrochloride salt, was washed with THF and diethyl ether and dried. There was thus obtained pure, the hydrochloride salt of the required product which was not basified.

g. The product gave the following NMR data: ($CD_3SOCD_3$) 3.99 (s, 3H), 4.03 (s, 3H), 7.39 (s, 1H), 7.58–7.63 (m, 2H), 8.03 (s, 1H), 8.14 (s, 1H), 8.38 (s, 1H), 8.77 (s, 1H), 11.62 (broad s, 1H);
and the following analytical data: Found C, 56.7; H, 4.6; N, 19.6; $C_{17}H_{15}N_5O_2$ 1HCl 0.05$H_2O$ requires C, 56.9; H, 4.5; N, 19.5%.

h. The product gave the following NMR data: ($CD_3SOCD_3$) 4.0 (s, 3H), 4.05 (s, 3H), 7.41 (s, 1H), 7.78 (m, 1H), 8.0 (d, 1H), 8.28 (d, 1H), 8.47 (s, 1H), 8.85 (s, 1H), 11.78 (broad s, 1H); and the following analytical data: Found C, 53.6; H, 4.2; N, 23.4; $C_{16}H_{14}N_6O_2$ 1HCl requires C, 53.6; H, 4.2; N, 23.4%.

i. The product gave the following NMR data: ($CD_3SOCD_3$) 3.99 (s, 3H), 4.03 (s, 3H), 7.38 (s, 1H), 8.14 (d, 1H), 8.43 (s, 1H), 8.52 (d, 1H), 8.73 (m, 1H), 8.82 (s, 1H), 9.41 (s, 1H), 11.7 (broad s, 1H); and the following analytical data:
Found C, 54.1; H, 3.7; N, 14.6; $C_{17}H_{14}N_4O_2S$ 1HCl

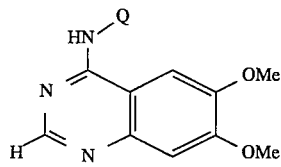

| Example 2 Compd. No. | Q | m.p. (°C.) |
|---|---|---|

0.05$H_2O$ requires C, 54.3; H, 4.05; N, 14.9%.

j. The product gave the following NMR data: ($CD_3SOCD_3$ + $CF_3CO_2D$) 4.01 (s, 6H), 7.39 (s, 1H), 7.83–7.89 (m, 2H), 8.08–8.17 (m, 1H), 8.33 (s, 1H), 8.72 (s, 1H);
and the following analytical data: Found C, 51.2; H, 3.7; N, 18.4; $C_{16}H_{13}N_5O_2S$ 1HCl requires C, 51.1; H, 3.75; N, 18.6%.

k. THF was used in place of isopropanol and the reaction mixture was heated to reflux for 3 hours. The product gave the following NMR data: ($CD_3SOCD_3$) 2.05 (m, 2H), 2.88 (m, 4H), 3.93 (s, 3H), 3.96 (s, 3H), 7.16 (s, 1H), 7.22 (d, 1H), 7.48 (m, 1H), 7.66 (broad s, 1H), 7.84 (s, 1H), 8.42 (s, 1H), 9.39 (broad s, 1H);
and the following analytical data: Found C, 71.2; H, 6.0; N, 13.0; $C_{19}H_{19}N_3O_2$ requires C, 71.0; H, 6.0; N, 13.1%.

l. THF was used in place of isopropanol and the reaction mixture was heated to reflux for 3 hours. The product gave the following NMR data: ($CD_3SOCD_3$) 1.70 (m, 4H), 2.60 (m, 2H), 2.80 (m, 2H), 3.92 (s, 6H), 7.02 (d, 1H), 7.08–7.18 (m, 3H), 7.81 (s, 1H), 8.26 (s, 1H), 9.25 (broad s, 1H);
and the following analytical data: Found C, 70.8; H, 6.2; N, 12.2; $C_{20}H_{21}N_3O_2$ 0.15$H_2O$ requires C, 71.0; H, 6.35; N, 12.4%.

EXAMPLE 3

Ammonium formate (4.53 g) was added to a stirred mixture of 6-nitro-4-(6-quinolylamino)quinazoline (5.7 g), 10% palladium-on-charcoal catalyst (0.5 g), methanol (75 ml) and ethanol (75 ml). The mixture was stirred at ambient temperature for 3 hours. The mixture was filtered and the filtrate was evaporated. The residue was partitioned between methylene chloride and water and basified to pH11 by the addition of a dilute aqueous sodium hydroxide solution. The organic phase was dried ($MgSO_4$) and evaporated. The residue was triturated under diethyl ether. There was thus obtained 6-amino-4-(6-quinolylamino)quinazoline (2.84 g, 55%), m.p. 248°–25020 C.;

NMR Spectrum: ($CD_3SOCD_3$) 5.7 (broad s, 1H), 7.29 (m, 1H), 7.44 (d, 1H), 7.51 (t, 1H), 7.58 (d, 1H), 8.0 (d, 1H), 8.18 (m, 1H), 8.30 (m, 1H), 8.43 (s, 1H), 8.57 (d, 1H), 8.78 (m, 1H);

Elemental Analysis: Found C, 63.9; H, 5.2; N, 21.4; $C_{17}H_{13}N_5$ 1.9$H_2O$ requires C, 63.5; H, 5.3; N, 21.8%.

The 6-nitro-4-(6-quinolylamino)quinazoline used as starting material was obtained as follows:

Using an analogous procedure to that described in the first paragraph of the portion of Example 1 which is concerned with the preparation of starting materials, 5-nitroanthranilic acid was reacted with formamide to give 6-nitroquinazolin-4-one in 82% yield, m.p. 268°–271° C.

A mixture of 6-nitroquinazolin-4-one (10 g), phosphorus pentachloride (16.4 g) and phosphoryl chloride (20 ml) was heated to reflux for 2 hours. The mixture was cooled to ambient temperature and hexane (700 ml) was added. The mixture was stored at 0° C. for 16 hours. The precipitate was isolated and partitioned between chloroform (700 ml) and water (550 ml). The aqueous layer was basified by the addition of 2N aqueous sodium hydroxide solution and extracted with chloroform (2×200 ml). The combined organic solutions were dried ($MgSO_4$) and evaporated.

There was thus obtained 4-chloro-6-nitroquinazoline (1.6 g) which was used without further purification.

Using an analogous procedure to that described in Example 1, 4-chloro-6-nitroquinazoline was reacted with 6-aminoquinoline to give 6-nitro-4-(6-quinolylamino-)quinazoline in 86% yield, m.p. >300° C.;

NMR Spectrum: ($CD_3SOCD_3$) 7.51 (m, 1H), 7.98 (d, 1H), 8.06 (d, 1H), 8.21 (m, 1H), 8.35 (m, 1H), 8.52 (d, 1H), 8.58 (m, 1H), 8.78 (s, 1H), 8.84 (m, 1H), 9.72 (d, 1H), 10.69 (broad s, 1H);

Elemental Analysis: Found C, 63.4; H, 3.2; N, 21.5; $C_{17}H_{11}N_5O_2$ 0.25$H_2O$ requires C, 63.4; H, 3.6; N, 21.7%.

EXAMPLE 4

Acetic anhydride (0.11 g) was added to a stirred solution of 6-amino-4-(6-quinolylamino)quinazoline (0.3 g) in DMA (3 ml). The mixture was stirred at ambient temperature for 18 hours. The mixture was evaporated and the residue was triturated under ethyl acetate. There was thus obtained 6-acetamido-4-(6-quinolylamino)quinazoline (0.282 g, 82%), m.p. >300° C.;

NMR Spectrum: ($CD_3SOCD_3$) 2.23 (s, 3H), 7.58 (m, 1H), 7.86 (d, 1H), 7.96 (m, 1H), 8.09 (d, 1H), 8.28 (m, 1H), 8.40 (m, 1H), 8.56 (d, 1H), 8.67 (s, 1H), 8.83 (d, 1H), 8.89 (m, 1H), 10.16 (s, 1H), 10.33 (broad s, 1H);

Elemental Analysis: Found C, 68.8; H, 4.4; N, 21.1; $C_{19}H_{15}N_5O$ 0.1$H_2O$ requires C, 68.9; H, 4.6; N, 21.1%.

EXAMPLE 5

A mixture of 4-chloro-6-piperidinoquinazoline (0.371 g), 5-aminoindole (0.198 g) and isopropanol (5 ml) was stirred and heated to reflux for 2 hours. The mixture was cooled to ambient temperature and allowed to stand for 16 hours. The precipitate was filtered off and washed in turn with isopropanol and diethyl ether. There was thus obtained 4-(5-indolylamino)-6-piperidinoquinazoline hydrochloride (0.51 g, 91%), m.p. 247°–250° C.;

NMR Spectrum: ($CD_3SOCD_3$) 1.50 (m, 6H), 3.31 (m, 4H), 6.35 (m, 1H), 7.13 (m, 1H), 7.28 (m, 1H), 7.34 (d, 1H), 7.63 (d, 1H), 7.65 (m, 1H), 7.81 (s, 1H), 8.49 (s, 1H), 11.15 (broad s, 1H), 11.21 (broad s, 1H);

Elemental Analysis: Found C, 67.0; H, 5.9; N, 18.4; $C_{21}H_{21}N_5$ 0.9HCl requires C, 67.0 H, 5.8; N, 18.6%.

The 4-chloro-6-piperidinoquinazoline used as a starting material was obtained as follows:

A mixture of 5-chloro-2-nitrobenzoic acid (13.7 g), piperidine (27 ml) and DMA (100 ml) was stirred and heated to 120° C. for 18 hours. The mixture was evaporated. The residue was dissolved in water and the solution was basified to pH10 by the addition of 2N aqueous sodium hydroxide solution. The solution was extracted with ethyl acetate. The aqueous layer was acidified to pH2 by the addition of concentrated hydrochloric acid and extracted with ethyl acetate. The organic layer was dried (Mg$SO_4$) and evaporated to give 2-nitro-5-piperidinobenzoic acid (16.25 g), m.p. 130°–140° C.

A mixture of a portion (10 g) of the material so obtained, 10% palladium-on-charcoal catalyst (1 g) and DMA (150 ml) was heated to 40° C. and stirred under an atmosphere of hydrogen for 4 hours. The mixture was filtered and the filtrate was evaporated. There was thus obtained 5-piperidinoanthranilic acid as an oil (12.1 g) which was used without further purification.

A mixture of the material so obtained and formamide (50 ml) was stirred and heated to 170° C. for 90 minutes. The mixture was allowed to cool to ambient temperature. The precipitate was isolated, washed with formamide and with diethyl ether and dried. There was thus obtained 6-piperidinoquinazolin-4-one (5.95 g), m.p. 160°–166° C.

Phosphoryl chloride (5.37 g) was added to a stirred mixture of 6-piperidinoquinazoline (4 g), N,N-dimethylaniline (3.81 g) and toluene (70 ml). The mixture was heated to reflux for 2 hours. The mixture was allowed to cool to ambient temperature, diluted with toluene (80 ml) and extracted with dilute aqueous ammonium hydroxide solution. The organic phase was dried (Mg$SO_4$) and evaporated. The residue was purified by column chromatography using increasingly polar mixtures of methylene chloride and ethyl acetate as eluent. There was thus obtained 4-chloro-6-piperidinoquinazoline as a solid (2.01 g).

EXAMPLE 6

2-Chloroacetyl chloride (0.123 g) was added to a mixture of 6-amino-4-(6-quinolylamino)quinazoline (0.3 g), triethylamine (0.11 g) and DMF (3 ml). The mixture was stirred at ambient temperature for 18 hours. A precipitate was deposited. The mixture was evaporated, ethyl acetate was added to the residue and the solid was collected. The solid was dissolved in a 5:1 mixture of methylene chloride and methanol (total volume 120 ml) and the solution was washed with water. The organic layer was dried (Mg$SO_4$) and evaporated. There was thus obtained 6-(2-chloroacetamido)-4-(6-quinolylamino)quinazoline (0.12 g, 32%), m.p. >300° C.;

NMR Spectrum: ($CD_3SOCD_3$) 4.38 (s, 2H), 7.51 (m, 1H), 7.82 (d, 1H), 7.90 (d, 1H), 8.03 (d, 1H), 8.19 (m, 1H), 8.33 (d, 1H), 8.48 (d, 1H), 8.62 (s, 1H), 8.82 (m, 1H), 10.18 (broad s, 1H), 10.63 (broad s, 1H);

Elemental Analysis: Found C, 59.1; H, 4.4; N, 17.7; $C_{19}H_{14}ClN_5O$ 1.25$H_2O$ requires C, 59.1; H, 4.3; N, 18.1%.

EXAMPLE 7

A mixture of 4-chloro-6,7-dimethoxyquinazoline (0.15 g), 7-aminoquinoline (*J. Amer. Chem. Soc.*, 1946, 68, 149; 0.13 g) and isopropanol (6 ml) was stirred and heated to reflux for 2 hours. The mixture was cooled to ambient temperature. The precipitate was isolated and washed in turn with isopropanol and acetone. There was thus obtained 6,7-dimethoxy-4-(7-quinolylamino)quinazoline hydrochloride (0.036 g, 14%), m.p. 248°–249° C. (decomposes);

NMR Spectrum: ($CD_3SOCD_3$) 3.96 (s, 3H), 4.01 (s, 3H), 7.45 (s, 1H), 7.73 (m, 1H), 8.20 (d, 1H), 8.28 (m, 1H), 8.50 (s, 1H), 8.70 (d, 1H), 8.72 (d, 1H), 8.90 (s, 1H), 9.05 (m, 1H), 11.70 (broad s, 1H);

Elemental Analysis: Found C, 58.4; H, 4.5; N, 14.1; $C_{19}H_{16}N_4O_2$ 1.6HCl requires C, 58.4; H, 4.5; N, 14.3%.

EXAMPLE 8

Using an analogous procedure to that described in Example 7, 4-chloro-6,7-dimethoxyquinazoline was reacted with the appropriate heterocyclic amine to give the compounds described in the following table, the structures of which were confirmed by proton magnetic resonance spectroscopy and by elemental analysis.

TABLE II

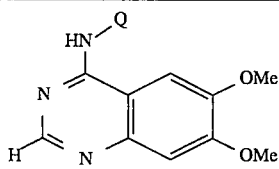

| Example 8 Compd. No. | Q | m.p. (°C.) |
|---|---|---|
| 1[a] | 6-methoxyquinolin-8-yl | — |
| 2[b] | 3-quinolyl | 242–245 |
| 3[c] | 5-benzimidazolyl | >250 |
| 4[d] | 1H-benzotriazol-4-yl | >250 |
| 5[e] | 1H-indazol-6-yl | 246–248 (decomposes) |
| 6[f] | 1H-indazol-7-yl | 279–280 |
| 7[g] | 1H-indazol-4-yl | 242–244 |
| 8[h] | 2 methylindol-5-yl | 118–140 |
| 9[i] | 2,3-dimethylindol-5-yl | >126 |
| 10[j] | 1-methylindol-5-yl | 252–253 |
| 11[k] | 6-indolyl | >240 |
| 12[l] | 4-indolyl | >250 |
| 13[m] | 4-indanyl | 243–245 |
| 14[n] | 6-carboxyindan-5-yl | >250 |
| 15[a] | 3-carboxynaphth-2-yl | — |

Notes a. The purity of this product was determined by conventional high performance liquid chromatographic (HPLC) methods.
b. The product gave the following NMR data: $(CD_3SOCD_3)$ 4.01 (s, 3H), 4.07 (s, 3H), 7.43 (s, 1H), 7.69 (m, 1H), 7.83 (m, 1H), 8.08 (m, 2H), 8.58 (s, 1H), 8.81 (d, 1H), 8.91 (s, 1H), 9.39 (d, 1H); and the following analytical data: Found C, 56.7; H, 4.4; N, 13.5; $C_{19}H_{16}N_4O_2$ 2HCl requires C, 56.7; H, 4.4; N, 13.5%.
c. The product gave the following NMR data: $(CD_3SOCD_3)$ 4.02 (s, 3H), 4.05 (s, 3H), 7.40 (s, 1H), 7.83 (m, 2H), 8.22 (s, 1H), 8.45 (s, 1H), 8.80 (s, 1H), 9.15 (s, 1H), 11.55 (broad s, 1H); and the following analytical data: Found C, 51.4; H, 4.4; N, 17.5; $C_{17}H_{15}N_5O_2$ 2HCl requires C, 51.8; H, 4.35; N, 17.8%.
d. 4-Amino-1H-benzotriazole is disclosed in J. Org. Chem., 1992, 57, 190. The product gave the following NMR data: $(CD_3SOCD_3)$ 4.05 (s, 3H), 4.06 (s, 3H), 7.47 (s, 1H), 7.56 (m, 1H), 7.62 (d, 1H), 8.01 (d, 1H), 8.49 (s, 1H), 8.79 (s, 1H), 12.15 (broad s, 1H); and the following analytical data: Found C, 53.2; H, 4.5; N, 22.4; $C_{16}H_{14}N_6O_2$ 1HCl 0.15$(CH_3)_2$ CHOH requires C, 53.7; H, 4.4; N, 22.8%.
e. THF was used in place of isopropanol and the reaction mixture was heated to reflux for 40 hours. The product gave the following NMR data: $(CD_3SOCD_3)$ 3.99 (s, 3H), 4.03 (s, 3H), 7.91 (s, 1H), 7.45 (m, 1H), 7.83 (d, 1H), 7.95 (s, 1H), 8.10 (s, 1H), 8.44 (s, 1H), 8.82 (s, 1H), 11.59 (broad s, 1H), 13.3 (broad s, 1H); and the following analytical data: Found C, 56.5; H, 4.5; N, 19.1; $C_{17}H_{15}N_5O_2$ 1HCl 0.15$H_2O$ requires C, 56.6; H, 4.6; N, 19.4%.
f. 7-Amino-1H-indazole is disclosed in J. Amer. Chem. Soc., 1943, 65, 1804–1805. THF was used in place of isopropanol and the reaction mixture was heated to reflux for 40 hours. The product gave the following NMR data: $(CD_3SOCD_3$ & $CD_3OD)$ 4.09 (s, 6H), 7.28 (t, 1H), 7.32 (s, 1H), 7.48 (d, 1H), 7.86 (d, 1H), 8.12 (s, 1H), 8.16 (s, 1H), 8.64 (s, 1H); and the following analytical data: Found C, 57.0; H, 4.5; N, 19.4; $C_{17}H_{15}N_5O_2$ 1HCl requires C, 57.1; H, 4.5; N, 19.6%.
g. 4-Amino-1H-indazole is disclosed in J. Chem. Soc., 1955, 2412–2418. THF was used in place of isopropanol and the reaction mixture was heated to reflux for 40 hours. The product gave the following NMR data: $(CD_3SOCD_3)$ 4.0 (s, 3H), 4.03 (s, 3H), 7.24 (d, 1H), 7.45 (t, 1H), 7.46 (s, 1H), 7.57 (d, 1H), 7.99 (s, 1H), 8.47 (s, 1H), 8.73 (s, 1H), 11.86 (broad s, 1H), 13.25 (broad s, 1H); and the following analytical data: Found C, 56.4; H, 4.4; N, 19.0; $C_{17}H_{15}N_5O_2$ 1HCl 0.25$H_2O$ requires C, 56.4; H, 4.6; N, 19.3%.
h. 5-Amino-2-methylindole is disclosed in Chem. Abs., 90, 137852 g. THF was used in place of isopropanol and the reaction mixture was heated to reflux for 28 hours. The reaction mixture was evaporated and the residue was purified by column chromatography using a 19:1 mixture of methylene chloride and methanol as eluent. The product gave the following NMR data:

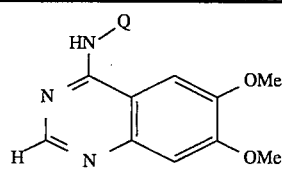

| Example 8 Compd. No. | Q | m.p. (°C.) |
|---|---|---|

$(CD_3SOCD_3)$ 2.39 (s, 3H), 3.92 (s, 3H), 3.94 (s, 3H), 6.12 (s, 1H), 7.14 (s, 1H), 7.25 (s, 2H), 7.68 (s, 1H), 7.85 (s, 1H), 8.33 (s, 1H), 9.37 (broad s, 1H), 10.84 (broad s, 1H); and the following analytical data: Found C, 68.1; H, 5.4; N, 16.4; $C_{19}H_{18}N_4O_2$ requires C, 68.2; H, 5.4; N, 16.8%.
i. 5-Amino-2,3-dimethylindole is disclosed in Tet. Lett., 1991, 32, 5035–8. THF was used in place of isopropanol and the reaction mixture was heated to reflux for 24 hours. The mixture was evaporated and the residue was partitioned between methylene chloride and a saturated aqueous sodium bicarbonate solution. The organic phase was dried and evaporated. The residue was purified by column chromatography using a 19:1 mixture of methylene chloride and methanol as eluent. The product gave the following NMR data: $(CD_3SOCD_3)$ 2.18 (s, 3H), 2.33 (s, 1H), 3.96 (s, 3H), 3.98 (s, 3H), 7.17 (s, 1H), 7.24 (d, 1H), 7.30 (m, 1H), 7.57 (d, 1H), 7.88 (s, 1H), 8.35 (s, 1H), 9.4 (broad s, 1H), 10.6 (broad s, 1H); and the following analytical data: Found C, 68.8; H, 5.7; N, 15.9; $C_{20}H_{20}N_4O_2$ requires C, 68.9; H, 5.8; N, 16.1%.
j. 5-Amino-1-methylindole is disclosed in Zh. Obshch. Khim., 1959, 29, 317. The reaction product was obtained in an impure state and was purified as follows. The material was partitioned between methylene chloride and 1N aqueous sodium hydroxide. The organic phase was dried and evaporated. The residue was purified by column chromatography using increasingly polar mixtures of methylene chloride and methanol as eluent. The product gave the following NMR data:
$(CD_3SOCD_3)$ 3.81 (s, 3H), 3.93 (s, 3H), 3.97 (s, 3H), 6.42 (d, 1H), 7.16 (s, 1H), 7.32 (d, 1H), 7.36–7.48 (m, 2H), 7.85–7.92 (m, 2H), 8.37 (s, 1H), 9.44 (broad s, 1H);
and the following analytical data: Found C, 68.4; H, 5.4; N, 16.5; $C_{19}H_{18}N_4O_2$ requires C, 68.2; H, 5.4; N, 16.8%.
k. 6-Aminoindole is disclosed in J. Amer. Chem. Soc., 1954, 76, 5149. The reaction product was suspended in 1N aqueous sodium hydroxide solution. The solid was isolated, washed with water and dried. The solid so obtained was purified by column chromatography using a 19:1 mixture of methylene chloride and methanol as eluent. The product gave the following NMR data: $(CD_3SOCD_3)$ 3.97 (s, 3H), 4.0 (s, 3H), 6.42 (d, 1H), 7.20 (s, 1H), 7.30 (m, 1H), 7.32 (d, 1H), 7.52 (d, 1H), 7.90 (s, 1H), 8.0 (s, 1H), 8.42 (s, 1H), 9.43 (broad s, 1H), 11.05 (broad s, 1H);
and the following analytical data: Found C, 67.7; H, 5.1; N, 17.2; $C_{18}H_{16}N_4O_2$ requires C, 67.5; H, 5.0; N, 17.5%.
l. 4-Aminoindole is disclosed in J. Org. Chem., 1968, 33, 192–7. The product gave the following NMR data: $(CD_3SOCD_3)$ 4.0 (s, 3H), 4.01 (s, 3H), 6.31 (m, 1H), 7.12 (m, 1H), 7.19 (m, 1H), 7.37–7.47 (m, 3H), 8.34 (s, 1H), 8.67 (s, 1H), 11.37 (broad s, 1H), 11.58 (broad s, 1H); and the following analytical data: Found C, 60.7; H, 4.9; N, 15.3; $C_{18}H_{16}N_4O_2$ 1HCl requires C, 60.6; H, 4.8; N, 15.7%.
m. 4-Aminoindane is disclosed in J. Amer. Chem. Soc., 1955, 77, 979–983. The product gave the following NMR data: $(CD_3SOCD_3)$ 1.94–2.10 (m, 2H), 2.73–3.00 (m, 4H), 3.98 (s, 3H), 4.0 (s, 3H), 7.1–7.3 (m, 3H), 7.42 (s, 1H), 8.37 (s, 1H), 8.74 (s, 1H), 11.62 (broad s, 1H); and the following analytical data: Found C, 63.9; H, 5.9; N, 11.2; $C_{19}H_{19}N_3O_2$ 1HCl requires C, 63.8; H, 5.7; N, 11.7%.
n. The product gave the following NMR data: $(CD_3SOCD_3)$ 2.08–2.18 (m, 2H), 2.92–3.02 (m, 2H), 4.0 (s, 6H), 7.41 (s, 1H), 7.89 (s, 1H), 7.93 (s, 1H), 7.98 (s, 1H), 8.82 (s, 1H), 12.0 (broad s, 1H); and the following analytical data: Found C, 59.7; H, 6.2; N, 9.2; $C_{20}H_{19}N_3O_4$ 1$H_2O$ 1$(CH_3)_2$ CHOH requires C, 59.8; H, 6.1; N, 9.1%.

The 5-amino-6-carboxyindane used as a starting material was obtained as follows:

A mixture of 5-acetamido-6-bromoindane (*Berichte*, 59, 1913; 91.7 g), cuprous cyanide (43.3 g) and NMP (460 ml) was stirred and heated to 130° C. for 1 hour. The mixture was cooled to ambient temperature and poured into a mixture of water (1.8 L) and aqueous ammonium hydroxide (0.88 g/ml, 1.2 L). The precipitate was isolated and washed with water. The solid was partitioned between ethyl acetate and dilute aqueous ammonium hydroxide. The organic phase was washed with water and with dilute aqueous hydrochloric acid, dried ($MgSO_4$) and evaporated. There was thus obtained 5-acetamido-6-cyanoindane (29.7 g), m.p. 172°–174° C.

A mixture of a portion (12 g) of the product so obtained, glacial acetic acid (150 ml) and concentrated hydrochloric acid (450 ml) was stirred and heated to 100° C. for 16 hours. The mixture was cooled to ambient temperature and neutralised to pH5 by the dropwise addition of concentrated (40%) aqueous sodium hydroxide solution followed by the portionwise addition of sodium bicarbonate. The mixture was extracted with ethyl acetate. The organic phase was washed with brine, dried ($MgSO_4$) and evaporated. There was thus obtained 5-amino-6-carboxyindane (9.2 g).

EXAMPLE 9

Sodium bis(trimethylsilyl)amide (1M in THF, 1.1 ml) was added to a solution of 8-aminoisoquinoline (*J. Chem. Soc.*, 1956, 4191; 0.158 g) in THF (8 ml) and the mixture was stirred at ambient temperature for 5 minutes. 4-Chloro-6,7-dimethoxyquinazoline (0.224 g) was added and the mixture was stirred at ambient temperature for 24 hours. The mixture was partitioned between methylene chloride and water. The organic phase was washed with brine, dried ($MgSO_4$) and evaporated. The residue was purified by column chromatography using a 19:1 mixture of methylene chloride and methanol as eluent. There was thus obtained 6,7-dimethoxy-4-(8-isoquinolylamino)quinazoline (0.15 g, 45%), m.p. 216°–219° C.;

NMR Spectrum: ($CD_3SOCD_3$) 3.98 (s, 3H), 4.0 (s, 3H), 7.24 (s, 1H), 7.73–7.93 (m, 4H), 8.0 (s, 1H), 8.28 (s, 1H), 8.52 (d, 1H), 9.3 (s, 1H), 9.97 (broad s, 1H);

Elemental Analysis: Found C, 68.2; H, 4.8; N, 16.7; $C_{19}H_{16}N_4O_2$ requires C, 68.7; H, 4.85; N, 16.9%.

EXAMPLE 10

Using an analogous procedure to that described in Example 9, 2-aminoquinoline was reacted with 4-chloro-6,7-dimethoxyquinazoline to give 6,7-dimethoxy-4-(2-quinolylamino)quinazoline in 56% yield, m.p. 215°–216° C.;

NMR Spectrum: ($CD_3SOCD_3$) 4.07 (s, 3H), 4.11 (s, 3H), 7.36 (s, 1H), 7.60 (m, 1H), 7.83 (m, 1H), 8.03 (m, 2H), 8.20 (s, 1H), 8.45 (d, 1H), 8.60 (broad s, 1H), 8.72 (s, 1), 10.7 (broad s, 1H);

Elemental Analysis: Found C, 68.5; H, 4.8; N, 16.6; $C_{19}H_{16}N_4O_2$ requires C, 68.7; H, 4.85; N, 16.9%.

EXAMPLE 11

Using an analogous procedure to that described in Example 9, 1-aminoisoquinoline was reacted with 4-chloro-6,7-dimethoxyquinazoline to give 6,7-dimethoxy-4-(1-isoquinolylamino)quinazoline in 13% yield, m.p. 198°–199° C.;

NMR Spectrum: ($CD_3SOCD_3$) 3.96 (s, 3H), 4.03 (s, 3H), 7.14 (d, 1H), 7.21 (s, 1H), 7.73 (m, 1H), 7.82 (m, 2H), 7.91 (d, 1H), 8.11 (s, 1H), 8.63 (s, 1H), 8.99 (d, 1H);

Elemental Analysis: Found C, 68.8; H, 4.8; N, 16.7; $C_{19}H_{16}N_4O_2$ requires C, 68.7; H, 4.85; N, 16.9%.

EXAMPLE 12

A mixture of 4-chloro-6,7-methylenedioxyquinazoline (0.209 g), 4-aminobenzo[c][2,1,3]thiadiazole (0.151 g) and THF (8 ml) was stirred and heated to reflux for 72 hours. The mixture was cooled to ambient temperature and the precipitate was isolated, washed with THF and diethyl ether and dried. There was thus obtained 4-(benzo[c][2,1,3]thiadiazol-4-ylamino)-6,7-methylenedioxyquinazoline hydrochloride (0.32 g, 89%), m.p. 281°–283° C.;

NMR Spectrum: ($CD_3SOCD_3$) 6.42 (s, 2H), 7.50 (s, 1H), 7.86 (d, 2H), 8.12 (t, 1H), 8.47 (s, 1H), 8.69 (s, 1H), 11.90 (broad s, 1H);

Elemental Analysis: Found C, 50.3; H, 2.7; N, 19.2; $C_{15}H_9N_5O_2S$ 1HCl requires C, 50.1; H, 2.8; N, 19.5%.

The 4-chloro-6,7-methylenedioxyquinazoline used as a starting material was obtained from 4,5-methylenedioxyanthranilic acid using analogous procedures to those described in the portion of Example 1 which is concerned with the preparation of starting materials. The intermediate 6,7-methylenedioxyquinazolin-4-one is described in *J. Med. Chem.*, 1970, 13, 867.

EXAMPLE 13

The procedure described in Example 12 was repeated except that 6-amino-1H-indazole was used in place of 4-aminobenzo[c][2,1,3]thiadiazole. There was thus obtained 4-(1H-indazol-6-yl)-6,7-methylenedioxyquinazoline hydrochloride in 79% yield, m.p. >300° C.;

NMR Spectrum: ($CD_3SOCD_3$) 6.34 (s, 2H), 7.33 (s, 1H), 7.40 (m, 1H), 7.79 (d, 1H), 7.94 (s, 1H), 8.05 (s, 1H), 8.27 (s, 1H), 8.78 (s, 1H);

Elemental Analysis: Found C, 55.8; H, 3.9; N, 19.3; $C_{16}H_{11}N_5O_2$ 1HCl 0.2$H_2O$ 0.2THF requires C, 56.1; H, 3.9; N, 19.5%.

EXAMPLE 14

A mixture of 4-(1H-indazol-5-ylamino)-6-nitroquinazoline (10.7 g), 10% palladium-on-charcoal catalyst (2 g) and ethanol (500 ml) was stirred at ambient temperature under an atmosphere of hydrogen for 8 hours. The mixture was filtered and the filtrate was evaporated. The residual solid was triturated in ethanol and reisolated. There was thus obtained 6-amino-4-(1H-indazol-5-ylamino)quinazoline (3.0 g, 31%), m.p. >270° C.;

NMR Spectrum: ($CD_3SOCD_3$) 5.5 (broad s, 2H), 7.23 (m, 1H), 7.38 (d, 1H), 7.52 (m, 2H), 7.67 (m, 1H), 8.05 (s, 1H), 8.22 (d, 1H), 8.27 (s, 1H), 9.35 (s, 1H), 12.95 (broad s, 1H);

Elemental Analysis: Found C, 62.8; H, 4.2; N, 29.0; $C_{15}H_{12}N_6$ 0.6$H_2O$ requires C, 62.8; H, 4.6; N, 29.3%.

The 4-(1H-indazol-5-ylamino)-6-nitroquinazoline used as a starting material was obtained as follows:

Using an analogous procedure to that described in Example 1, 4-chloro-6-nitroquinazoline was reacted with 5-amino-1H-indazole to give in turn 4-(1H-indazol-5-ylamino)-6-nitroquinazoline hydrochloride in 68% yield, m.p. 289°–291° C., and the free base in quantitative yield.

EXAMPLE 15

Using an analogous procedure to that described in Example 5, 4-chloro-6-dimethylaminoquinazoline was reacted with 5-amino-1H-indazole to give 6-dimethylamino-4-(1H-indazol-5-ylamino)quinazoline hydrochloride in 92% yield, m.p. >300° C.;

NMR Spectrum: ($CD_3SOCD_3$) 3.17 (s, 6H), 7.56 (m, 1H), 7.61–7.80 (m, 4H), 8.02 (s, 1H), 8.16 (s, 1H), 8.68 (s, 1H), 11.29 (s, 1H), 13.2 (broad s, 1H);

Elemental Analysis: Found C, 60.2; H, 6.4; N, 21.0; $C_{17}H_{16}N_6$ 1HCl 1($CH_3$)$_2$CHOH requires C, 59.9; H, 6.2; N, 21.0%.

The 4-chloro-6-dimethylaminoquinazoline used as a starting material was obtained as follows:

A mixture of 5-fluoroanthranilic acid (13.2 g) and formamide (27 ml) was stirred and heated to 160° C. for 90 minutes and to 180° C. for 60 minutes. The mixture was cooled to ambient temperature. The mixture was triturated under water. The solid so obtained was isolated, washed with water and with diethyl ether and dried. There was thus obtained 6-fluoroquinazolin-4-one (12.5 g, 84%).

A mixture of the product so obtained and a saturated solution of dimethylamine in NMP (50 ml) was heated to 180° C. in a sealed glass tube for 48 hours. The mixture was cooled to ambient temperature and evaporated. The residue was triturated under water. The solid so obtained was washed with water and with diethyl ether and dried. There was thus obtained 6-dimethylaminoquinazolin-4-one (11.5 g, 80%), m.p. 229°–233° C.

Phosphoryl chloride (11 ml) was added to a stirred mixture of 6-dimethylaminoquinazolin-4-one (11 g), N,N-dimethylaniline (13 ml) and toluene (200 ml). The mixture was heated to reflux for 2 hours. The mixture was cooled to ambient temperature, diluted with toluene (50 ml) and washed with dilute aqueous ammonium hydroxide solution. The organic phase was dried ($MgSO_4$) and evaporated. The residue was purified by column chromatography using methylene chloride as eluent. There was thus obtained 4-chloro-6-dimethylaminoquinazoline (5.8 g, 53%).

EXAMPLE 16

Using an analogous procedure to that described in Example 5, 4-chloro-6-(1-pyrrolidinyl)quinazoline was reacted with 5-amino-1H-indazole to give 4-(1H-indazol-5-ylamino)-6-(1-pyrrolidinyl)quinazoline hydrochloride in 78% yield, m.p. 271°–273° C.;

NMR Spectrum: ($CD_3SOCD_3$) 2.04 (m, 4H), 3.43 (m, 4H), 7.46 (m, 1H), 7.60 (m, 1H), 7.62 (d, 1H), 7.67 (d, 1H), 7.86 (d, 1H), 8.03 (s, 1H), 8.14 (s, 1H), 8.62 (s, 1H), 11.6 (broad s, 1H), 13.28 (broad s, 1H);

Elemental Analysis: Found C, 60.6; H, 5.4; N, 22.0; $C_{19}H_{18}N_6$ 1HCl 0.5$H_2O$ requires C, 60.7; H, 5.3; N, 22.3%.

The 4-chloro-6-(1-pyrrolidinyl)quinazoline used as a starting material was obtained as follows:

Using analogous procedures to those described in the portion of Example 5 which is concerned with the preparation of starting materials, 5-chloro-2-nitrobenzoic acid was reacted with pyrrolidine and the resultant product was converted in turn to 5-(1-pyrrolidinyl)anthranilic acid, 6-(1-pyrrolidinyl)quinazolin-4-one and 4-chloro-6-(1-pyrrolidinyl)quinazoline in an overall yield of 40%.

EXAMPLE 17

Using an analogous procedure to that described in Example 5, 4-chloro-7-fluoroquinazoline was reacted with 5-amino-1H-indazole to give 7-fluoro-4-(1H-indazol-5-ylamino)quinazoline hydrochloride in 70% yield, m.p. >300° C.;

NMR Spectrum: ($CD_3SOCD_3$) 7.62 (m, 2H), 7.76 (d, 1H), 7.80 (d, 1H), 8.08 (s, 1H), 8.18 (s, 1H), 8.90 (s, 1H), 9.12 (m, 1H), 11.9 (broad s, 1H), 13.2 (broad s, 1H);

Elemental Analysis: Found C, 57.0; H, 3.5; N, 21.6; $C_{15}H_{10}FN_5$ 1HCl 0.06($CH_3$)$_2$CHOH requires C, 57.0; H, 3.6; N, 21.9%.

The 4-chloro-7-fluoroquinazoline used as a starting material was obtained as follows:

Using analogous procedures to those described in the portion of Example 1 which is concerned with the preparation of starting materials, 4-fluoroanthranilic acid was converted in turn into 7-fluoroquinazolin-4-one and 4-chloro-7-fluoroquinazoline in an overall yield of 72%.

EXAMPLE 18

A mixture of 7-fluoro-4-(1H-indazol-5-ylamino)quinazoline hydrochloride (0.15 g), piperazine (0.233 g) and DMA (4 ml) was stirred and heated to reflux for 4 hours. The mixture was evaporated and the residue was triturated under water. The resultant solid was washed with water and dried. There was thus obtained 4-(1H-indazol-5-ylamino)-7-(1-piperazinyl)quinazoline (0.097 g, 52%), m.p. >280° C.;

NMR Spectrum: ($CD_3SOCD_3$) 2.9 (m, 8H), 3.55 (s, 1H), 6.95 (d, 1H), 7.38 (m, 1H), 7.53 (d, 1H), 7.68 (m, 1H), 8.06 (s, 1H), 8.22 (d, 1H), 8.39 (d, 1H), 8.42 (s, 1H), 9.58 (broad s, 1H), 13.0 (broad s, 1H);

Elemental Analysis: Found C, 59.6; H, 5.7; N, 25.7; $C_{19}H_{19}N_7$ 1$H_2O$ 1HF requires C, 59.5; H, 5.7; N, 25.6%.

EXAMPLE 19

A mixture of 7-fluoro-4-(1H-indazol-5-ylamino)quinazoline hydrochloride (0.15 g), sodium methanethiolate (0.102 g) and DMA (3 ml) was stirred and heated to 100° C. for 1 hour. The mixture was cooled to ambient temperature and acidified by the addition of glacial acetic acid. The mixture was evaporated and the residue was purified by column chromatography using increasingly polar mixtures of methylene chloride and methanol as eluent. There was thus obtained 4-(1H-indazol-5-ylamino)-7-methylthioquinazoline (0.11 g, 67%), m.p. 259°–262° C.;

NMR Spectrum: ($CD_3SOCD_3$) 2.61 (s, 3H), 7.49 (d, 1H), 7.50 (m, 1H), 7.58 (s, 1H), 7.66 (m, 1H), 8.09 (s, 1H), 8.20 (d, 1H), 8.44 (d, 1H), 8.50 (s, 1H), 9.81 (broad s, 1H), 13.02 (broad s, 1H);

Elemental Analysis: Found C, 61.0; H, 4.6; N, 21.7; $C_{16}H_{13}N_5S$ 0.5$H_2O$ requires C, 60.7; H, 4.4; N, 22.1%.

EXAMPLE 20

The procedure described in Example 12 was repeated except that 5-aminoindole was used in place of 4-aminobenzo[c][2,1,3]thiadiazole. There was thus obtained 4-(5-indolyl)-6,7-methylenedioxyquinazoline hydrochloride in 95% yield, m.p. >300° C.;

NMR Spectrum: ($CD_3SOCD_3$) 6.37 (s, 2H), 6.47 (broad s, 1H), 7.28 (m, 1H), 7.38–7.50 (m, 3H), 7.77 (d, 1H), 8.37 (s, 1H), 8.70 (s, 1H), 11.2 (broad s, 1H), 11.29 (broad s, 1H);

Elemental Analysis: Found C, 60.2; H, 3.9; N, 16.2; $C_{17}H_{12}N_4O_2$ 1HCl requires C, 59.9; H, 3.85; N, 16.4%.

EXAMPLE 21

Using an analogous procedure to that described in Example 5, 4-chloro-7-fluoroquinazoline was reacted with 5-aminoindole to give 7-fluoro-4-(5-indolylamino)quinazoline hydrochloride in 65% yield;

NMR Spectrum: ($CD_3SOCD_3$) 6.50 (t, 1H), 7.32 (m, 1H), 7.44 (m, 1H), 7.52 (d, 1H), 7.74 (d, 1H), 7.75 (m, 1H), 7.84 (d, 1H), 8.83 (s, 1H), 9.02 (m, 1H), 11.3 (broad s, 1H), 11.8 (broad s, 1H);

Elemental Analysis: Found C, 60.7; H, 3.9; N, 17.1; $C_{16}H_{11}FN_4$ 1HCl 0.1$(CH_3)_2$CHOH requires C, 61.0; H, 4.0; N, 17.5%.

EXAMPLE 22

Using an analogous procedure to that described in Example 5, 4-chloro-6-nitroquinazoline was reacted with 5-aminoindole to give 4-(5-indolylamino)-6-nitroquinazoline hydrochloride in 53% yield, m.p. 300° C.;

NMR Spectrum: ($CD_3SOCD_3$) 6.51 (m, 1H), 7.32–7.58 (m, 3H), 7.89 (d, 1H), 8.13 (d, 1H), 8.77 (m, 1H), 8.90 (s, 1H), 9.86 (d, 1H), 11.32 (broad s, 1H), 12.0 (broad s, 1H);

Elemental Analysis: Found C, 56.2; H, 3.6; N, 19.4; $C_{16}H_{11}N_5O_2$ 1HCl requires C, 56.4; H, 3.9; N, 19.6%.

EXAMPLE 23

Using an analogous procedure to that described in Example 5, 4-chloro-6-dimethylaminoquinazoline was reacted with 5-aminoindole to give 6-dimethylamino-4-(5-indolylamino)quinazoline hydrochloride in 96% yield, m.p. 221°–226° C.;

NMR Spectrum: ($CD_3SOCD_3$) 3.13 (s, 6H), 6.51 (m, 1H), 7.28 (m, 1H), 7.42 (m, 1H), 7.51 (d, 1H), 7.58–7.82 (m, 4H), 8.62 (s, 1H), 11.25 (m, 2H);

Elemental Analysis: Found C, 63.1; H, 6.5; N, 17.2; $C_{18}H_{17}N_5$ 1HCl 1$(CH_3)_2$CHOH requires C, 63.1; H, 6.5; N, 17.5%.

EXAMPLE 24

Using an analogous procedure to that described in Example 5, 4-chloro-6-(1-pyrrolidinyl)quinazoline was reacted with 5-aminoindole to give 4-(5-indolylamino)-6-(1-pyrrolidinyl)quinazoline in 84% yield;

NMR Spectrum: ($CD_3SOCD_3$) 2.05 (t, 4H), 3.43 (t, 4H), 6.49 (t, 1H), 7.30 (m, 1H), 7.4–7.65 (m, 3H), 7.79 (d, 1H), 7.82 (d, 1H), 8.59 (s, 1H), 11.2 (broad m, 2H);

Elemental Analysis: Found C, 63.9; H, 6.2; N, 17.7; $C_{20}H_{19}N_5$ 1HCl 0.5$H_2O$ 0.2$(CH_3)_2$CHOH requires C, 63.8; H, 5.8; N, 18.1%.

EXAMPLE 25

The procedure described in Example 12 was repeated except that 6-aminoindole was used in place of 4-aminobenzo[c][2,1,3]thiadiazole. There was thus obtained 4-(6-indolyl)-6,7-methylenedioxyquinazoline hydrochloride in 94% yield, m.p. >300° C.;

NMR Spectrum: ($CD_3SOCD_3$) 6.37 (s, 2H), 6.46 (broad s, 1H), 7.25 (m, 1H), 7.38–7.42 (m, 2H), 7.59 (d, 1H), 7.75 (s, 1H), 8.36 (s, 1H), 8.73 (s, 1H), 11.12 (broad s, 1H), 11.30 (broad s, 1H);

Elemental Analysis: Found C, 60.1; H, 3.9; N, 16.2; $C_{17}H_{12}N_4O_2$ 1HCl requires C, 59.9; H, 3.85; N, 16.4%.

EXAMPLE 26

A mixture of 4-chloro-6,7-dimethoxyquinazoline (0.225 g), 5-aminobenzo[c][2,1,3]thiadiazole (*Chemical Abstracts*, Vol. 49, 3170c; 0.151 g) and THF (15 ml) was stirred and heated to reflux for 44 hours. The mixture was cooled to ambient temperature, acetone (30 ml) was added and the precipitate was isolated, washed with acetone and dried. There was thus obtained 4-(benzo[c][2,1,3]thiadiazol-5-ylamino)-6,7-dimethoxyquinazoline hydrochloride (0.135 g, 38%), m.p. 255° C.;

NMR Spectrum: ($CD_3SOCD_3$) 4.03 (s, 3H), 4.06 (s, 3H), 7.32 (s, 1H), 8.11 (m, 1H), 8.19 (m, 2H), 8.59 (d, 1H), 8.90 (s, 1H);

Elemental Analysis: Found C, 51.0; H, 3.6; N, 18.3; $C_{16}H_{13}N_5O_2S$ 1HCl requires C, 51.1; H, 3.75; N, 18.6%.

EXAMPLE 27

A mixture of 4-chloro-7-fluoro-6-methoxyquinazoline (0.32 g), 5-aminoindole (0.197 g) and isopropanol (5 ml) was stirred and heated to reflux for 90 minutes. The mixture was cooled to ambient temperature and the precipitate was isolated, washed with isopropanol and with water and dried. There was thus obtained 7-fluoro-4-(5-indolylamino)-6-methoxyquinazoline hydrochloride (0.504 g, 97%), m.p. 268°–270° C.;

NMR Spectrum: ($CD_3SOCD_3$) 4.09 (s, 3H), 6.50 (m, 1H), 7.34 (m, 1H), 7.42 (t, 1H), 7.48 (d, 1H), 7.33 (d, 1H), 7.78 (d, 1H), 8.60 (s, 1H);

Elemental Analysis: Found C, 58.6; H, 4.1; N, 15.8; $C_{17}H_{13}N_4FO$ 1.1HCl requires C, 58.5, H, 4.0; N, 16.1%.

The 4-chloro-7-fluoro-6-methoxyquinazoline used as a starting material was obtained as follows:

Sulphuric acid (concentrated, 120 ml) was stirred and heated to 90° C. 2-Fluoro-5-trifluoromethylphenol (27 g) was added portionwise during 25 minutes. The mixture was heated to 120° C. for 10 minutes. The mixture was cooled to ambient temperature and poured onto a mixture of ice and water. The precipitate was isolated, washed with water and dried. There was thus obtained 4-fluoro-3-hydroxybenzoic acid (14.3 g, 61%).

A mixture of the material so obtained, methyl iodide (38.3 g), potassium carbonate (37.3 g) and DMA (200 ml) was stirred at ambient temperature for 16 hours. The mixture was partitioned between ethyl acetate and water. The organic phase was washed with water, dried ($MgSO_4$) and evaporated. The residue was purified by column chromatography using increasingly polar mixtures of petroleum ether (b.p. 40°–60° C.) and methylene chloride as eluent. There was thus obtained methyl 4-fluoro-3-methoxybenzoate (14.8 g).

Concentrated nitric acid (70%, 4.8 ml) was added dropwise during 20 minutes to a stirred mixture of methyl 4-fluoro-3-methoxybenzoate (14 g) and concentrated sulphuric acid (140 ml) which had been cooled to −10° C. The mixture was allowed to warm to 5° C. and was stirred at that temperature for 15 minutes. The mixture was poured onto ice and extracted with ethyl acetate. The organic phase was washed with water, dried ($MgSO_4$) and evaporated. The residue was purified by column chromatography using increasingly polar mixtures of hexane and methylene chloride as eluent. There was thus obtained methyl 4-fluoro-5-methoxy-2-nitrobenzoate (11.8 g).

A mixture of a portion (10.3 g) of the material so obtained, 10% palladium-on-charcoal catalyst (1 g) and ethanol (500 ml) was stirred under an atmosphere pressure of hydrogen for 3 hours. The mixture was filtered and the filtrate was evaporated. There was thus obtained 4-fluoro-5-methoxy-anthranilic acid methyl ester (9 g).

Using analogous procedures to those described in the portion of Example 1 which is concerned with the preparation of starting materials, 4-fluoro-5-methoxy-anthranilic acid methyl ester was converted into 4-chloro-7-fluoro-6-methoxyquinazoline in 30% yield.

EXAMPLE 28

A mixture of 4-(5-indolylamino)-6-nitroquinazoline hydrochloride (4.3 g) and a saturated aqueous sodium bicarbonate solution was stirred at ambient temperature for 1 hour. The mixture was filtered. The solid was suspended in ethanol (200 ml) and 10% palladium-on-charcoal catalyst (1 g) was added. The mixture was stirred under an atmosphere of hydrogen for 7 hours. The mixture was filtered and the filtrate was evaporated. There was thus obtained 6-amino-4-(5-indolylamino)quinazoline (3.3 g, 86%), m.p. 200° C. (decomposes);

NMR Spectrum: ($CD_3SOCD_3$) 6.1 (broad s, 1H), 6.5 (m, 1H), 7.3 (m, 1H), 7.4 (m, 2H), 7.5 (d, 1H), 7.6 (m, 2H), 7.8 (m, 1H), 8.6 (s, 1H), 10.9 (broad s, 1H), 11.2 (broad s, 1H).

EXAMPLE 29

4-Chlorobutyryl chloride (0.32 ml) was added to a stirred solution of 6-amino-4-(5-indolylamino)quinazoline (0.62 g) in DMA (2 ml) and the mixture was stirred at ambient temperature for 2 hours. The mixture was evaporated and the residue was purified by column chromatography using a 19:1 mixture of methylene chloride and methanol as eluent. There was thus obtained 6-(4-chlorobutyramido)-4-(5-indolylamino)quinazoline (0.85 g).

A solution of the material so obtained in DMA (5 ml) was added to a stirred suspension of sodium hydride (60% dispersion in mineral oil, 0.269 g; from which the oil was washed with hexane) in DMA (1 ml). The mixture was stirred at ambient temperature for 1 hour. Ethanol (1 ml) and acetic acid (2 ml) were added and the mixture was evaporated. The residue was triturated under water. The solid so obtained was isolated and dried. The solid was purified by column chromatography using a 50:1 mixture of methylene chloride and methanol as eluent. There was thus obtained 4-(5-indolylamino)-6-(2-oxopyrrolidin-1-yl)quinazoline (0.062 g, 8%);

NMR Spectrum: ($CD_3SOCD_3$) 2.08–2.25 (m, 2H), 2.57 (t, 2H), 4.02 (t, 2H), 6.44 (broad s, 1H), 7.3–7.45 (m, 3H), 7.74 (d, 1H), 7.86 (d, 1H), 8.22 (d, 1H), 8.42 (s, 1H), 8.57 (m, 1H), 9.71 (s, 1H), 11.1 (broad s, 1H);

Elemental Analysis: Found C, 65.3; H, 5.3; N, 18.6; $C_{20}H_{17}N_5O$ 1.5$H_2O$ requires C, 64.9; H, 5.4; N, 18.9%.

EXAMPLE 30

A mixture of 4-chloro-6,7-dimethoxyquinazoline (0.17 g), 5-aminoindole-3-carboxylic acid (*J. Org. Chem.*, 1962, 27, 496; 0.128 g) and THF (15 ml) was stirred and heated to reflux for 16 hours. A further portion of 4-chloro-6,7-dimethoxyquinazoline (0.09 g) was added and the mixture was heated to reflux for 16 hours. The mixture was cooled to ambient temperature. The precipitate was isolated, washed with THF and with acetone and dried. There was thus obtained 4-(3-carboxyindol-5-ylamino)-6,7-dimethoxyquinazoline hydrochloride (0.16 g, 53%), m.p. 197°–201° C. (decomposes);

NMR Spectrum: ($CD_3SOCD_3$) 4.0 (s, 3H), 4.03 (s, 3H), 7.39 (s, 1H), 7.50 (m, 1H), 7.58 (d, 1H), 8.09 (d, 1H), 8.19 (d, 1H), 8.29 (s, 1H), 8.73 (s, 1H), 11.3 (s, 1H), 12.04 (broad s, 1H);

Elemental Analysis: Found C, 54.5; H, 4.9; N, 13.1; $C_{19}H_{16}N_4O_4$ 1HCl 1$H_2O$ requires C, 54.5; H, 4.6; N, 13.4%.

EXAMPLE 31

A mixture of 4-chloro-6,7-dimethoxyquinazoline (0.225 g), 5-amino-3-cyanoindole (0.157 g) and THF (15 ml) was stirred and heated to reflux for 20 hours. The mixture was cooled to ambient temperature and acetone (30 ml) was added. The precipitate was isolated, washed with acetone and dried. There was thus obtained 4-(3-cyanoindol-5-ylamino)-6,7-dimethoxyquinazoline hydrochloride (0.16 g, 39%), m.p. 250°–252° C. (decomposes);

NMR Spectrum: ($CD3SOCD_3$) 4.0 (s, 3H), 4.02 (s, 3H), 7.33 (s, 1H), 7.58 (m, 1H), 7.68 (d, 1H), 7.96 (m, 1H), 8.30 (s, 1H), 8.32 (d, 1H), 8.82 (s, 1H), 11.38 (s, 1H), 12.45 (broad s, 1H);

Elemental Analysis: Found C, 59.4; H, 4.7; N, 17.1; $C_{19}H_{15}N_5O_2$ 1HCl 0.25$H_2O$ 0.3$C_4H_8O$ requires C, 59.5; H, 4.7; N, 17.1%.

The 5-amino-3-cyanoindole used as a starting material was obtained as follows:

A mixture of 3-cyano-5-nitroindole (*J. Med. Chem.*, 1964, 7, 213; 0.5 g) iron powder (0.46 g), ethanol (6 ml), water (3 ml) and concentrated hydrochloric acid (1 drop) was stirred and heated to reflux for 16 hours. The mixture was cooled to ambient temperature and evaporated. The residue was purified by column chromatography using a 9:1 mixture of methylene chloride and ethyl acetate as eluent. There was thus obtained 5-amino-3-cyanoindole (0.26 g, 62%), m.p. 165°–167° C.

EXAMPLE 32

A mixture of 4-chloro-6,7-dimethoxyquinazoline (0.45 g), ethyl 6-aminoindole-2-carboxylate (*Indian J. Chem.*, Sect. B, 1983, 22, 1205; 0.41 g) and THF (40 ml) was stirred and heated to reflux for 20 hours. The mixture was cooled to ambient temperature and the precipitate was isolated, washed with acetone and dried. There was thus obtained 6,7-dimethoxy-4-(2-ethoxycarbonylindol-6-ylamino)quinazoline hydrochloride (0.25 g, 29%), m.p. >250° C.;

NMR Spectrum: ($CD_3SOCD_3$) 1.36 (t, 3H), 4.01 (s, 3H), 4.02 (s, 3H), 4.37 (q, 2H), 7.20 (m, 1H), 7.32 (s, 1H), 7.39 (m, 1H), 7.78 ( d, 1H), 7.80 (s, 1H), 8.22 (s, 1H), 8.80 (s, 1H), 11.24 (s, 1H), 12.05 (broad s, 1H);

Elemental Analysis: Found 58.8; H, 4.8; N, 13.0; $C_{21}H_{20}N_4O_4$ 1HCl requires C, 58.8; H, 4.94; N, 13.1%.

EXAMPLE 33

The following illustrate representative pharmaceutical dosage forms containing the compound of formula I, or a pharmaceutically-acceptable salt thereof (hereafter compound X), for therapeutic or prophylactic use in humans:

| (a) | Tablet I | mg/tablet |
|---|---|---|
| | Compound X | 100 |
| | Lactose Ph. Eur | 182.75 |
| | Croscarmellose sodium | 12.0 |
| | Maize starch paste (5% w/v paste) | 2.25 |
| | Magnesium stearate | 3.0 |

-continued

| (b) | Tablet II | | mg/tablet |
|---|---|---|---|
| | Compound X | | 50 |
| | Lactose Ph. Eur | | 223.75 |
| | Croscarmellose sodium | | 6.0 |
| | Maize starch | | 15.0 |
| | Polyvinylpyrrolidone (5% w/v paste) | | 2.25 |
| | Magnesium stearate | | 3.0 |
| (c) | Tablet III | | mg/tablet |
| | Compound X | | 1.0 |
| | Lactose Ph. Eur | | 93.25 |
| | Croscarmellose sodium | | 4.0 |
| | Maize starch paste (5% w/v paste) | | 0.75 |
| | Magnesium stearate | | 1.0 |
| (d) | Capsule | | mg/capsule |
| | Compound X | | 10 |
| | Lactose Ph. Eur | | 488.5 |
| | Magnesium stearate | | 1.5 |
| (e) | Injection I | | (50 mg/ml) |
| | Compound X | | 5.0% w/v |
| | 1M Sodium hydroxide solution | | 15.0% v/v |
| | 0.1M Hydrochloric acid (to adjust pH to 7.6) | | |
| | Polyethylene glycol 400 | | 4.5% w/v |
| | Water for injection to 100% | | |
| (f) | Injection II | | 10 mg/ml) |
| | Compound X | | 1.0% w/v |
| | Sodium phosphate BP | | 3.6% w/v |
| | 0.1M Sodium hydroxide solution | | 15.0% v/v |
| | Water for injection to 100% | | |
| (g) | Injection III | | (1 mg/ml, buffered to pH6) |
| | Compound X | | 0.1% w/v |
| | Sodium phosphate BP | | 2.26% w/v |
| | Citric acid | | 0.38% w/v |
| | Polyethylene glycol 400 | | 3.5% w/v |
| | Water for injection to 100% | | |

Note

The above formulations may be obtained by conventional procedures well known in the pharmaceutical art. The tablets (a)–(c) may be enteric coated by conventional means, for example to provide a coating of cellulose acetate phthalate.

We claim:

1. A quinazoline derivative of the formula I

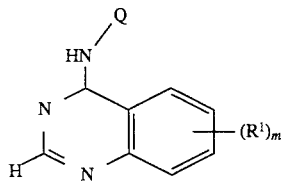

wherein m is 1, 2 or 3 and each $R^1$ is independently hydroxy, amino, ureido, hydroxyamino, trifluoromethoxy, (1–4C)alkyl, (1–4C)alkoxy, (1–3C)alkylenedioxy, (1–4C)alkylamino, di-[(1–4C)alkyl]amino, pyrrolidin-1-yl, piperidino, morpholino, piperazin-1-yl, 4-(1–4C)alkylpiperazin-1-yl, (1–4C)alkylthio, halogeno-(1–4C)alkyl, hydroxy-(1–4C)alkyl, (2–4C)alkanoyloxy-(1–4C)alkyl, (1–4C)alkoxy-(1–4C)alkyl, cyano-(1–4C)alkyl, amino-(1–4C)alkyl, (1–4C)alkylamino-(1–4C)alkyl, di-[(1–4C)alkyl]amino-(1–4C)alkyl, piperidino-(1–4C)alkyl, morpholino-(1–4C)alkyl, piperazin-1-yl-(1–4C)alkyl, 4-(1–4C)alkylpiperazin-1-yl-(1–4C)alkyl, hydroxy-(2–4C)alkoxy-(1–4C)alkyl, (1–4C)alkoxy-(2–4C)alkoxy-(1–4C)alkyl, hydroxy-(2–4C)alkylamino-(1–4C)alkyl, (1–4C)alkoxy-(2–4C)alkylamino-(1–4C)alkyl, halogeno-(2–4C)alkoxy, hydroxy-(2–4C)alkoxy, (2–4C)alkanoyloxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, (2–4C)alkanoyloxy, hydroxy-(2–4C)alkanoyloxy, (1–4C)alkoxy-(2–4C)alkanoyloxy, phenyl-(1–4C)alkoxy, halogeno-(2–4C)alkylamino, hydroxy-(2–4C)alkylamino, (2–4C)alkanoyloxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, (2–4C)alkanoylamino, (1–4C)alkoxycarbonylamino, benzamido, 3-phenylureido, halogeno-(2–4C)alkanoylamino, hydroxy-(2–4C)alkanoylamino or (1–4C)alkoxy-(2–4C)alkanoylamino, and wherein said benzamido substituent or any phenyl group in a $R^1$ substituent may optionally bear one or two halogeno, (1–4C)alkyl or (1–4C)alkoxy substituents; and Q is a 9- or 10-membered bicyclic heterocyclic moiety, or a hydrogenated derivative thereof, containing one or two nitrogen heteroatoms and optionally containing a further heteroatom selected from nitrogen, oxygen and sulphur, which heterocyclic moiety, or a hydrogenated derivative thereof, may optionally bear one or two substituents selected from halogeno, hydroxy, oxo, amino, nitro, carbamoyl, (1–4C)alkyl, (1–4C)alkoxy, (1–4C)alkylamino, di-[(1–4C)alkyl]amino and (2–4C)alkanoylamino; or a pharmaceutically-acceptable salt thereof.

2. A quinazoline derivative of the formula I

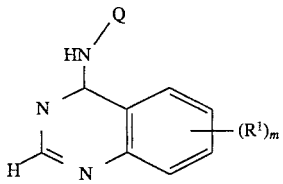

wherein m is 1, 2 or 3 and each $R^1$ is independently hydrogen, halogeno, nitro, hydroxy, amino, ureido, hydroxyamino, trifluoromethoxy, (1–4C)alkyl, (1–4C)alkoxy, (1–3C)alkylenedioxy, (1–4C)alkylamino, di-[1–4C)alkyl]amino, pyrrolidin-1-yl, piperidino, morpholino, piperazin-1-yl, 4-(1–4C)alkylpiperazin-1-yl, (1–4C)alkylthio, halogeno-(1–4C)alkyl, hydroxy-(1–4C)alkyl, (2–4C)alkanoyloxy-(1–4C)alkyl, (1–4C)alkoxy-(1–4C)alkyl, cyano-(1–4C)alkyl, amino-1–4C)alkyl, (1–4C)alkylamino-(1–4C)alkyl, di [(1–4C)alkyl ]amino-(1–4C)alkyl, piperidino-(1–4C)alkyl, morpholino-(1–4C)alkyl, piperazin-1-yl (1–4C)alkyl, 4-(1–4C)alkylpiperazin-1-yl-(1–4C)alkyl, hydroxy-(2–4C)alkoxy-(1–4C)alkyl, (1–4C)alkoxy(2–4C)alkoxy-(1–4C)alkyl, hydroxy-(2–4C)alkylamino-(1–4C)alkyl, (1–4C)alkoxy-(2–4C)alkylamino-(1–4C)alkyl, halogeno-(2–4C)alkoxy, hydroxy-(2–4C)alkoxy, (2–4C)alkanoyloxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, (2–4C)alkanoyloxy, hydroxy-(2–4C)alkanoyloxy, (1–4C)alkoxy-(2–4C)alkanoyloxy, phenyl-(1–4C)alkoxy, halogeno-(2–4C)alkylamino, hydroxy-(2–4C)alkylamino, (2–4C)alkanoyloxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, (2–4C)alkanoylamino, (1–4C)alkoxycarbonylamino, benzamido, 3-phenylureido, halogeno-(2–4C)alkanoylamino, hydroxy- (2–4C)alkanoylamino or (1–4C)alkoxy-(2–4C)alkanoylamino, and wherein said benzamido substituent or any phenyl group in a R¹ substituent may optionally bear one or two halogeno, (1–4C)alkyl or (1–4C)alkoxy substituents; and Q is a 9- or 10-membered bicyclic heterocyclic moiety, or a hydrogenated derivative thereof, containing one or two nitrogen heteroatoms and optionally containing a further heteroatom selected from nitrogen, oxygen and sulphur, which heterocyclic moiety, or a hydrogenated derivative thereof, may optionally bear one or two substituents selected from carboxy, (1–4C)alkoxycarbonyl, halogeno, hydroxy, oxo, amino, nitro, carbamoyl, (1–4C)alkyl, (1–4C)alkoxy, (1–4C)alkylamino, di-[(1–4C)alkyl]amino and (2–4C)alkanoylamino; or a pharmaceutically-acceptable salt thereof; except that 4-(4-quinazolinylamino)quinazoline is excluded.

3. A quinazoline derivative of the formula I

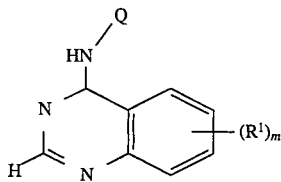

wherein M is 1, 2 or 3 and each R¹ is independently hydrogen, halogeno, nitro, hydroxy, amino, ureido, hydroxyamino, trifluoromethoxy, (1–4C)alkyl, (1–4C)alkoxy, (1–3C)alkylenedioxy, (1–4C)alkylamino, di-[1–4C)alkyl]amino, pyrrolidin-1-yl, piperidino, morpholino, piperazin-1-yl, 4-(1–4C)alkylpiperazin-1-yl, (1–4C)alkylthio, halogeno-(1–4C)alkyl, hydroxy-(1–4C)alkyl, (2–4C)alkanoyloxy-(1–4C)alkyl, (1–4C)alkoxy-(1–4C)alkyl, cyano-(1–4C)alkyl, amino-1–4C)alkyl, (1–4C)alkylamino-(1–4C)alkyl, di[(1–4C)alkyl]amino-(1–4C)alkyl, piperidino-(1–4C)alkyl, morpholino-(1–4C)alkyl, piperazin-1-yl-(1–4C)alkyl, 4-(1–4C)alkylpiperazin-1-yl-(1–4C)alkyl, hydroxy-(2–4C)alkoxy-(1–4C)alkyl, (1–4C)alkoxy-(2–4C)alkoxy-(1–4C)alkyl, hydroxy-(2–4C)alkylamino-(1–4C)alkyl, (1–4C)alkoxy-(2–4C)alkylamino-(1–4C)alkyl, halogeno-(2–4C)alkoxy, hydroxy-(2–4C)alkoxy, (2–4C)alkanoyloxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, (2–4C)alkanoyloxy, hydroxy-(2–4C)alkanoyloxy, (1–4C)alkoxy-(2–4C)alkanoyloxy, phenyl-(1–4C)alkoxy, halogeno-(2–4C)alkylamino, hydroxy-(2–4C)alkylamino, (2–4C)alkanoyloxy-(2–4C)alkylamino, (1–4C)alkoxy-(2–4C)alkylamino, amino-(2 –4C)alkylamino, (1–4C)alkylamino-(2 –4C)alkylamino, di-[(1–4C)alkyl]amino-(2–4C)alkylamino, (2–4C)alkanoylamino, (1–4C)alkoxycarbonylamino, benzamido, 3-phenylureido, halogeno-(2–4C)alkanoylamino, hydroxy-(2–4C)alkanoylamino, (1–4C)alkoxy-(2–4C)alkanoylamino, 2-oxopyrrolidin-1-yl or 2-oxopiperidin-1-yl, and wherein said benzamido substituent or any phenyl group in a R¹ substituent may optionally bear one or two halogeno, (1–4C)alkyl or (1–4C)alkoxy substituents; and Q is a 9- or 10-membered bicyclic heterocyclic moiety, or a hydrogenated derivative thereof, containing one or two nitrogen heteroatoms and optionally containing a further heteroatom selected from nitrogen, oxygen and sulphur, which heterocyclic moiety, or a hydrogenated derivative thereof, may optionally bear one or two substituents selected from cyano, carboxy, (1–4C)alkoxycarbonyl, halogeno, hydroxy, oxo, amino, nitro, carbamoyl, (1–4C)alkyl, (1–4C)alkoxy, (1–4C)alkylamino, di-[ (1–4C)alkyl]amino and (2–4C)alkanoylamino; or a pharmaceutically-acceptable salt thereof; except that 4-(4-quinazolinylamino)quinazoline is excluded.

4. A quinazoline derivative of the formula I as claimed in claim 1 or claim 2 wherein m is 1, 2 or 3 and each R¹ is independently hydroxy, amino, fluoro, chloro, nitro, methyl, ethyl, methoxy, ethoxy, propoxy, isopropoxy, butoxy, methylenedioxy, ethylenedioxy, methylamino, ethylamino, dimethylamino, diethylamino, pyrrolidin-1-yl, piperidino, morpholino, piperazin-1-yl, 4-methylpiperazin-1-yl, methylthio, ethylthio, acetamido, propionamido or 2-chloroacetamido; and Q is indolyl, 1H-benzimidazolyl, 1H-indazolyl, benzoxazolyl, benzothiazolyl, 1H-benzotriazolyl, benzo[c]furazanyl, benzo[c][2,1,3]thiadiazolyl, quinolyl, isoquinolyl, cinnolinyl, quinazolinyl or, quinoxalinyl, which may optionally bear one or two substituents selected from fluoro, chloro, hydroxy, amino, carboxy, methyl, ethyl, methoxy, ethoxy, methylamino, dimethylamino, acetamido, methoxycarbonyl and ethoxycarbonyl; or a pharmaceutically-acceptable salt thereof.

5. A quinazoline derivative of the formula I as claimed in claim 1 or claim 2 wherein (R¹)ₘ is 6-hydroxy, 7-hydroxy, 6,7-dihydroxy, 6-amino, 7-amino, 6-fluoro, 7-fluoro, 6-chloro, 7-chloro, 6-nitro, 6-methoxy, 7-methoxy, 6,7-dimethoxy, 6,7-diethoxy, 6-hydroxy-7-methoxy, 6,7-methylenedioxy, 6,7-ethylenedioxy, 6-methylamino, 7-methylamino, 6-ethylamino, 6-dimethylamino, 7-dimethylamino, 6-diethylamino, 6-pyrrolidin-1-yl, 7-pyrrolidin-1-yl, 6-piperidino, 7-piperidino, 6-morpholino, 7-morpholino, 6-piperazin-1-yl, 7-piperazin-1-yl, 6-(4-methylpiperazin-1-yl), 7-(4-methylpiperazin-1-yl), 6-methylthio, 7-methylthio, 6-amino-7-methoxy, 6-amino-7-methylamino, 6-acetamido, 7-acetamido, 6-(2-chloroacetamido) or 7-(2-chloroacetamido); and Q is 4-, 5- or 6-indolyl, 1H-benzimidazol-4-yl, 1H-benzimidazol-5-yl, 1H-benzimidazol-6-yl, 1H-indazol-4-yl, 1H-indazol-5-yl, 1H-indazol-6-yl, 1H-indazol-7-yl, 5- or 6-benzoxazolyl, 5- or 6-benzothiazolyl, 1H-benzotriazol-4-yl, 1H-benzotriazol-5-yl, 1H-benzotriazol-6-yl, benzo[c][2,1,3]thiadiazol-4-yl, 2-, 3-, 4-, 5-, 6-, 7- or 8-quinolyl, 1-, 3-, 4-, 5-, 6-, 7- or 8-isoquinolyl, 4-, 5-, 6-, 7- or 8-cinnolinyl, 5-, 6-, 7- or 8-quinazolinyl or 2-, 5- or 6-quinoxalinyl, which may optionally bear one or two substituents selected from fluoro, chloro, methyl, ethyl and methoxy; or a pharmaceutically-acceptable salt thereof.

6. A quinazoline derivative of the formula I as claimed in claim 1 wherein (R¹)ₘ is 6-amino, 6,7-dimethoxy, 6-piperidino or 6-acetamido; and Q is 5-indolyl, 1H-indazol-5-yl, 6-benzothiazolyl, 1H-benzotriazol-5-yl, benzo[c][2,1,3] thiadiazol-4-yl, 5-quinolyl, 6-quinolyl, 8-quinolyl, 5-isoquinolyl or 5-quinoxalinyl; or a pharmaceutically-acceptable salt thereof.

7. A quinazoline derivative of the formula I as claimed in claim 1 selected from:

6,7-dimethoxy-4-(5-quinolylamino)quinazoline, 6,7-dimethoxy-4-(6-quinolylamino)quinazoline, 6,7-dimethoxy-4-(5-isoquinolylamino)quinazoline, 6,7-dimethoxy-4-(5-indolylamino)quinazoline, 6,7-dimethoxy-4-[(1H-indazol-5-yl)amino]quinazoline, 4-(6-benzothiazolylamino)-6,7-dimethoxyquinazoline and 4-[(benzo[c][2,1,3]thiadiazol-4-yl)amino]-6,7-dimethoxyquinazoline; or a pharmaceutically-acceptable acid-addition salt thereof.

8. A pharmaceutical composition which comprises a quinazoline derivative of the formula I, or a pharmaceutically-acceptable salt thereof, as claimed in any one of claims 1–7 in association with a pharmaceutically-acceptable diluent or carrier.

9. A method for producing an anti-cancer effect in a warm-blooded animal having a cancer which is sensitive to inhibition of the EGF-type of receptor tyrosine kinase enzymes which comprises administering to said animal an effective amount of a quinazoline derivative of the formula I, or a pharmaceutically-acceptable salt thereof, as claimed in any one of claims 4–7.

10. A method for producing an anti-proliferative effect in a warm-blooded animal having a cancer which is sensitive to inhibition of the EGF-type of receptor tyrosine kinase enzymes which comprises administering to said animal an effective amount of a quinazoline derivative of the formula I, or a pharmaceutically-acceptable salt thereof, as claimed in any one of claims 4–7.

11. A method for aiding the regression or palliation in a warm-blooded animal of a cancer which is sensitive to inhibition of the EGF-type of receptor tyrosine kinase enzymes which comprises administering to said animal an effective amount of a quinazoline derivative of the formula I, or a pharmaceutically-acceptable salt thereof, as claimed in any one of claims 4–7.

12. A method for producing in a warm-blooded animal an inhibitory effect against the EGF-type of receptor tyrosine kinase enzymes which comprises administering to said animal an effective amount of a quinazoline derivative of the formula I, or a pharmaceutically-acceptable salt thereof, as claimed in any one of claims 4–7.

* * * * *